(12) United States Patent
Clement et al.

(10) Patent No.: US 6,565,588 B1
(45) Date of Patent: May 20, 2003

(54) INTRALUMENAL MATERIAL REMOVAL USING AN EXPANDABLE CUTTING DEVICE

(75) Inventors: Thomas J. Clement, Redmond, WA (US); Edward I. Wulfman, Woodinville, WA (US); Craig E. Lawson, Redmond, WA (US)

(73) Assignee: Pathway Medical Technologies, Inc., Redmond, WA (US)

( * ) Notice: Subject to any disclaimer, the term of this patent is extended or adjusted under 35 U.S.C. 154(b) by 0 days.

(21) Appl. No.: 09/724,914

(22) Filed: Nov. 28, 2000

Related U.S. Application Data
(60) Provisional application No. 60/194,998, filed on Apr. 5, 2000.

(51) Int. Cl.[7] .......................... A61B 17/14; A61B 17/32
(52) U.S. Cl. ................... 606/180; 606/180; 606/159; 606/171; 604/22
(58) Field of Search .................. 606/1, 108, 159, 606/170, 171, 180; 604/22

(56) References Cited

U.S. PATENT DOCUMENTS

| | | | | |
|---|---|---|---|---|
| 3,854,916 A | * | 12/1974 | Dochterman | 200/38 R |
| 4,445,509 A | | 5/1984 | Auth | 128/305 |
| 4,631,052 A | | 12/1986 | Kensey | 604/22 |
| 4,700,705 A | | 10/1987 | Kensey et al. | 128/341 |
| 4,747,821 A | | 5/1988 | Kensey et al. | 604/22 |
| 4,886,061 A | | 12/1989 | Fischell et al. | 128/305 |
| 4,895,560 A | | 1/1990 | Papantonakos | 604/22 |
| 4,926,858 A | | 5/1990 | Gifford, III et al. | 606/159 |
| 4,966,604 A | | 10/1990 | Reiss | 606/159 |
| 4,990,134 A | | 2/1991 | Auth | 604/22 |
| 5,002,553 A | | 3/1991 | Shiber | 606/159 |
| 5,030,201 A | | 7/1991 | Palestrant | 604/22 |
| 5,042,984 A | | 8/1991 | Kensey et al. | 606/128 |
| 5,097,849 A | | 3/1992 | Kensey et al. | 128/898 |
| 5,100,425 A | | 3/1992 | Fischell et al. | 606/159 |
| 5,152,773 A | | 10/1992 | Redha | 606/159 |
| 5,154,724 A | | 10/1992 | Andrews | 606/159 |
| 5,158,564 A | | 10/1992 | Schnepp-Pesch et al. | 606/159 |
| 5,176,693 A | | 1/1993 | Pannek, Jr. | 606/159 |
| 5,192,291 A | | 3/1993 | Pannek, Jr. | 606/159 |
| 5,217,474 A | | 6/1993 | Zacca et al. | 606/159 |
| 5,224,945 A | | 7/1993 | Pannek, Jr. | 606/159 |
| 5,282,813 A | | 2/1994 | Redha | 606/159 |
| 5,308,354 A | | 5/1994 | Zacca et al. | 606/159 |
| 5,314,407 A | | 5/1994 | Auth et al. | 604/22 |
| 5,395,311 A | | 3/1995 | Andrews | 604/22 |

(List continued on next page.)

*Primary Examiner*—Glenn K. Dawson
*Assistant Examiner*—Michael G. Mendoza
(74) *Attorney, Agent, or Firm*—Ann W. Speckman; James E. Klaniecki

(57) ABSTRACT

Intralumenal material removal systems are provided using an advanceable, rotatable and expandable cutter assembly. The intralumenal material removal system includes a cutter assembly positionable in the lumen of a mammalian subject and operably connected to system controls. The cutter assembly comprises a distal cutting head and an adjustable cutting assembly that is axially advanceable by translating the drive shaft and rotatable by rotating the drive shaft. The adjustable cutting assembly is adjustable between a smaller diameter condition and a larger diameter condition. The cutter may thus be introduced to and withdrawn from the material removal site in a retracted, smaller diameter condition that facilitates translation and navigation of the device through various lumens. The adjustable cutting assembly may be selectively expanded at the material removal site to facilitate cutting, removal and aspiration of the occlusive material.

28 Claims, 14 Drawing Sheets

U.S. PATENT DOCUMENTS

| | | | |
|---|---|---|---|
| 5,417,703 A | 5/1995 | Brown et al. | 606/159 |
| 5,419,774 A | 5/1995 | Willard et al. | 604/22 |
| 5,423,754 A | 6/1995 | Cornelius et al. | 604/103 |
| 5,490,859 A | 2/1996 | Mische et al. | 606/159 |
| 5,540,707 A | 7/1996 | Ressemann et al. | 606/159 |
| 5,556,408 A | 9/1996 | Farhat | 606/180 |
| 5,658,301 A | 8/1997 | Lemaitre et al. | 606/159 |
| 5,667,490 A | 9/1997 | Keith et al. | 604/22 |
| 5,681,336 A | 10/1997 | Clement et al. | 606/159 |
| 5,695,507 A | 12/1997 | Auth et al. | 606/159 |
| RE35,787 E | 5/1998 | Nash et al. | 606/128 |
| 5,766,190 A | 6/1998 | Wulfman | 606/159 |
| 5,766,192 A | 6/1998 | Zacca | 606/159 |
| 5,792,157 A | 8/1998 | Mische et al. | 606/159 |
| 5,836,868 A | 11/1998 | Reesemann et al. | 606/159 |
| 5,843,103 A | 12/1998 | Wulfman | 606/159 |
| 5,849,023 A * | 12/1998 | Mericle | 606/167 |
| 5,879,361 A | 3/1999 | Nash | 606/159 |
| 5,897,567 A | 4/1999 | Ressemann et al. | 606/159 |
| 5,916,227 A | 6/1999 | Keith et al. | 606/159 |
| 5,938,670 A | 8/1999 | Keith et al. | 606/159 |
| 5,938,672 A | 8/1999 | Nash | 606/159 |
| 5,957,941 A | 9/1999 | Ream | 606/159 |
| 5,976,165 A | 11/1999 | Ball et al. | 606/180 |
| 6,015,420 A | 1/2000 | Wulfman et al. | 606/168 |
| 6,080,170 A | 6/2000 | Nash et al. | 606/159 |
| 6,096,054 A | 8/2000 | Wyzgala et al. | 606/170 |
| 6,146,395 A | 11/2000 | Kanz et al. | 606/159 |
| 6,156,046 A * | 12/2000 | Passafaro | |
| 6,156,048 A | 12/2000 | Wulfman et al. | 606/159 |
| 6,183,487 B1 | 2/2001 | Barry et al. | 606/159 |
| 6,217,549 B1 | 4/2001 | Selmon et al. | 604/106 |
| 6,312,438 B1 * | 11/2001 | Adams | 606/159 |

OTHER PUBLICATIONS

PCT International Search Report: In re Styx Medical, Inc.; International Application No. PCT/US01/11105, filed Apr. 4, 2001.

* cited by examiner

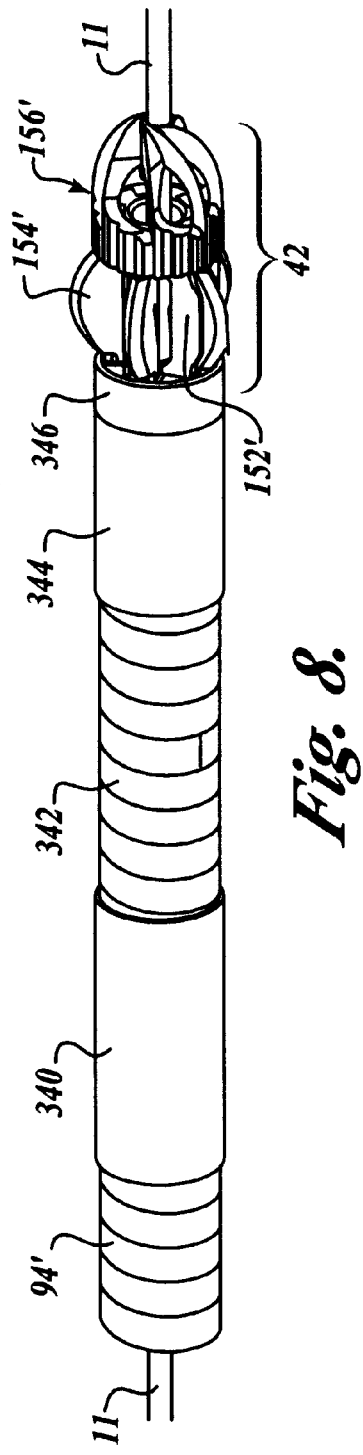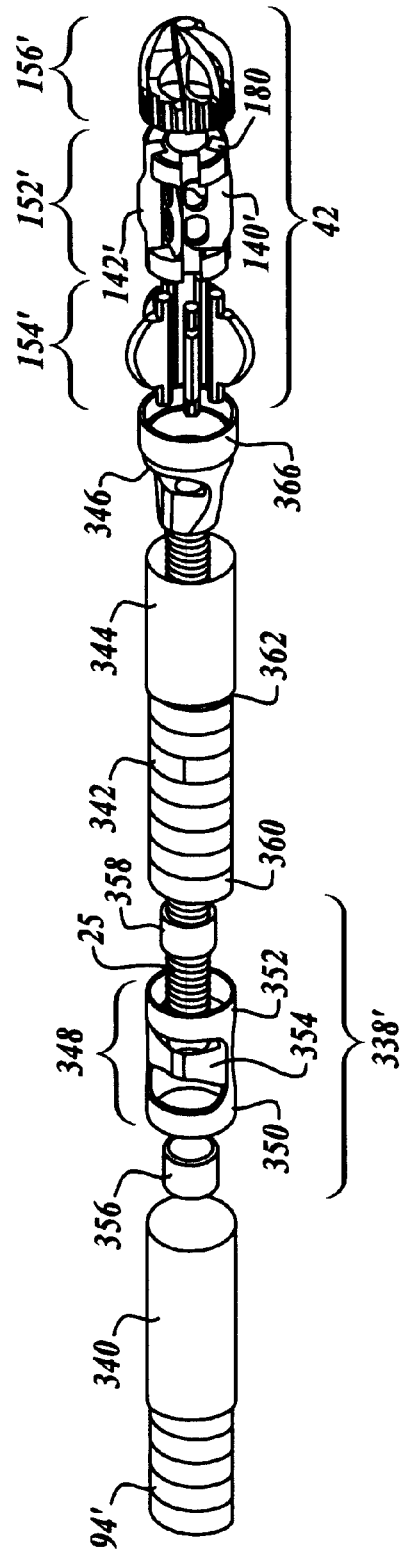
Fig. 8.
Fig. 9.

INTRALUMENAL MATERIAL REMOVAL USING AN EXPANDABLE CUTTING DEVICE

CROSS-REFERENCE TO RELATED APPLICATIONS

This application claims priority under 35 U.S.C. §119(e) to U.S. Provisional Patent Application No. 60/194,998, filed Apr. 5, 2000. The disclosure of the aforementioned application is herein incorporated by reference in its entirety.

BACKGROUND OF INVENTION

The present invention relates to systems and methods for removing material, such as obstructions and partial obstructions, from any body lumen of a mammalian subject, such as a blood vessel, particularly those in proximity to the heart, legs and kidneys, a portion of the gastrointestinal tract, any portion of the dural spaces associated with the spinal cord, or the like. More particularly, the present invention relates to systems and methods for removing material from a lumen of a mammalian subject using an advanceable and expandable cutter assembly.

DESCRIPTION OF PRIOR ART

Removal of atherosclerotic obstructions and partial obstructions using rotating cutter assemblies is a well established therapeutic intervention. Numerous atherectomy methods and devices have been conceived and developed. Most of these systems involve placement of a guide wire, a guiding catheter and a cutting device in proximity to an obstruction or partial obstruction in a blood vessel and then advancing and rotating the cutting device to cut or ablate the obstruction. Many of these devices operate using the principal of differential cutting, which provides cutting of relatively hard material, such as atherosclerotic material, but does not cut softer tissue, such as the walls of blood vessels.

The following U.S. Patents describe many types and specific features of atherectomy devices: U.S. Pat. Nos. 4,898,575; 5,927,902; 5,409,454; 5,976,165; 5,938,670; 5,843,103; 5,792,157; 5,667,490; 5,419,774; 5,417,713; 4,646,736; 4,990,134; 4,445,509; 5,681,336; 5,695,507; 5,827,229; 5,938,645; 5,957,941; 5,019,088; 4,887,613; 4,895,166; 5,314,407; 5,584,843; 4,966,604; 5,026,384; 5,019,089; 5,062,648; 5,101,682; 5,112,345; 5,192,291; 5,224,945; 4,732,154; 4,819,634; 4,883,458; 4,886,490; 4,894,051; 4,979,939; 5,002,553; 5,007,896; 5,024,651; 5,041,082; 5,135,531; 5,192,268; 5,306,244; 5,443,443; and 5,334,211. These U.S. Patents are incorporated by reference herein in their entireties.

Despite the many and varied approaches to atherectomy systems and methods exemplified by the U.S. patents cited above, many challenges remain in providing systems and methods for removing material from a lumen, such as a blood vessel, safely and reliably and without causing complications. The safety and reliability of the system is manifestly critical. Recovery of the debris generated during an atherectomy operation, or maceration of the debris to a particle size that will not produce additional blood vessel clogging or damage, is essential. The flexibility and size of the system is also an important feature. Control features and the ease of use of the system by a surgeon or other medical professional are additional important features.

One of the particular challenges of removing material from the interior of lumens is that the drive and cutter assemblies must be small enough and flexible enough to travel, over a guidewire, to a desired material removal site, such as the site of an obstruction or occlusion. Yet, the drive and cutter assemblies must be large enough and have structural integrity sufficient to operate reliably and effectively to cut or ablate the obstruction. Additionally, removal of the debris from the material removal site using an aspiration system is generally desirable. The drive and cutter assemblies therefore desirably incorporate a debris removal system as well.

The size and consistency of the material comprising the obstruction are frequently not well characterized prior to introduction of the material removal device. Thus, although devices and cutters having different sizes and properties may be provided, and may even be interchangeable on a materials removal system, it is difficult to ascertain which combination of features is desired in any particular operation prior to insertion of the device. The use of multiple cutter assemblies having different properties during a materials removal operation is inconvenient at best, since it requires removal of each independent device and interchange of the cutter assemblies, followed by reinsertion of the new cutter assembly, or of a new device entirely. Interchange and reinsertion of cutter assemblies is time consuming and generally deleterious to the health and condition of the patient undergoing the procedure.

Many different types of expandable cutters have been conceived in an effort to provide a cutter having a small diameter profile that may be delivered to and removed from the site of the desired material removal, and that is expandable at the site to provide a larger diameter cutter. The following U.S. Patents disclose various approaches to expandable cutter assemblies: U.S. Pat. Nos. 5,540,707; 5,192,291; 5,224,945; 5,766,192; 5,158,564; 4,895,560; 5,308,354; 5,030,201; 5,217,474; 5,100,425; and 4,966,604. These patents are incorporated by reference herein in their entireties.

Although many approaches to expandable cutter assemblies have been developed, none of these approaches has, to date, been known to be implemented in a commercially successful atherectomy system.

SUMMARY OF INVENTION

Methods and systems of the present invention involve placement of a material removal component, referred to herein as a "cutter" or "cutter assembly" within a lumen of a mammalian subject using conventional techniques, such as guidewires and guiding catheters. The intralumenal material removal system includes a cutter assembly positionable in the lumen of a mammalian subject and operably connected to system controls, mechanical and power systems by means of a rotating drive shaft and, generally a stationary, guide catheter. The cutter assembly preferably comprises a distal cutting or abrading head having one or more cutting and/or abrading surfaces that is advanceable by translating the drive shaft and rotatable by rotating the drive shaft. The cutter assembly may comprise two or more cutters having different properties.

According to a preferred embodiment of the present invention, the cutter assembly comprises a cutter that is adjustable between a smaller diameter condition, in which it may be guided to and withdrawn from the desired material removal site, and a larger diameter condition, in which it may be operated during a material removal operation. The cutter may thus be introduced to and withdrawn from the material removal site in a retracted, smaller diameter condition that facilitates translation and navigation of the device through various lumens, such as blood vessels. The expandable cutter may be selectively expanded at the material removal site to facilitate cutting, removal and aspiration of the material desired to be removed.

The material removal system preferably provides removal of debris, generally via aspiration through one or more material removal ports in the cutter assembly or another component in proximity to the cutter assembly. Debris generated during a material removal operation is removed by aspiration through the material removal ports and withdrawn through a sealed lumen formed, for example, between the cutter assembly drive shaft and a catheter. The sealed lumen is connectable to a vacuum source and aspirate collection system.

According to another preferred embodiment, the materials removal device of the present invention comprises dual cutting and/or abrading members, one of which is expandable and one of which has a fixed diameter. In one embodiment, a fixed diameter cutter is mounted distal to an expandable diameter cutter. The fixed diameter cutter may take any of a variety of configurations and, according to one embodiment, has a generally ovoid configuration and a plurality of cutting flutes. The fixed diameter cutter may also be provided with ports and/or cutouts that may be selectively employed as aspiration or infusion ports. The expandable diameter cutter, positioned proximal to the fixed diameter cutter, may also be provided with ports that may be selectively employed as aspiration or infusion ports.

In one embodiment, the cutter assembly drive shaft operates bidirectionally and the adjustable diameter cutter is expanded or retracted selectively and controllably upon rotation in opposite directions. Upon rotation of the drive shaft and dual cutter assembly in a first direction, the fixed diameter cutter is used as the primary cutting head and the expandable cutter remains in a smaller diameter condition, while upon rotation of the dual cutter assembly in a second direction, opposite the first, the expandable cutter is in a larger diameter condition and serves as the primary cutter. The present invention uses hydrodynamic, centrifugal and/or frictional forces to expand and contract the dual cutter assembly, thereby obviating the need for additional actuation systems, which add considerable complexity and rigidity to such systems.

Liquid infusion may be provided in proximity to the cutter assembly in addition to or alternatively to aspiration. Infusion of liquids may be used to provide additional liquids for materials removal or to deliver lubricating fluids, treatment agents, contrast agents, and the like. Infusion of fluids in proximity to the area of a material removal operation may be desirable because it tends to reduce the viscosity of the materials being removed, thus facilitating removal through relatively small diameter lumens. Infusion of liquids also desirably tends to reduce the volume of blood removed during the operation. According to one embodiment, a sealed lumen formed between the cutter assembly drive shaft and a catheter may alternatively and selectively be used as aspirate removal system and an infusion system. The sealed lumen may thus be selectively connectable to a vacuum source and aspirate collection system for aspiration, and an infusion source for infusion of liquids. Ports in or in proximity to the cutter assembly may be thus be employed, selectively, as aspiration and infusion ports.

According to another embodiment, an infusion system may be provided in addition to and independent of the aspiration system. In one embodiment, an infusion sleeve is provided that extends distal to the material removal element. The infusion sleeve is sealed for the length of the catheter and incorporates distal infusion ports. The infusion sleeve preferably extends through the lumen formed by the drive shaft and may be fixed, or preferably, translatable with respect to the dual cutter assembly.

BRIEF DESCRIPTION OF THE DRAWINGS

FIG. 2 shows one embodiment of the present invention highlighting the distal end of a primary sheath with an expandable cutter assembly in the expanded condition;

FIG. 3 shows an enlarged, partially cross-sectional perspective view of one embodiment of an expandable cutter assembly and associated connections with the drive shaft and flexible conduit catheter;

FIG. 8 shows additional embodiment of the present invention illustrating the distal end of a coiled metallic catheter with a cutter assembly in the expanded configuration;

FIG. 9 depicts the alternative embodiment in a exploded perspective;

DETAILED DESCRIPTION OF PREFERRED EMBODIMENTS

Figure 1A:
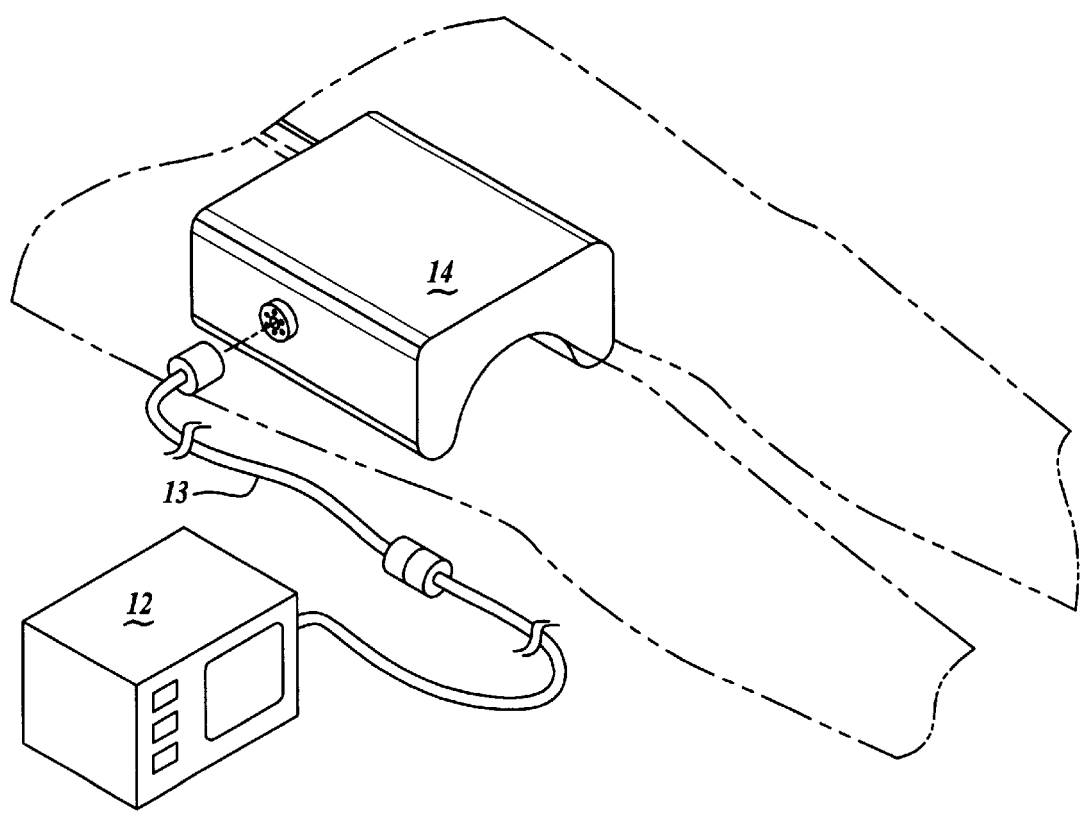
FIG. 1A shows a schematic diagram of one embodiment of a material removal advancer and control system of the present invention.

As used herein in the description of various components, "proximal" or "antegrade" refers to a direction toward the system controls and the operator, and "distal" or "retrograde" refers to the direction away from the system controls and the operator and toward a terminal end of the cutter assembly. In general, the material removal system of the present invention comprises a control unit attached to one end of a catheter assembly, a manifold assembly, a guiding catheter assembly and a cutter assembly positioned at the distal end of the material removal system. Exemplary material removal systems, components and subassemblies are disclosed and described in the U.S. Patents incorporated herein by reference.

The cutter assembly is translated over a guidewire to the material removal site, and is actuated at the material removal site to cut, grind or ablate, or otherwise remove, the occlusive material. The control unit, catheter assembly and manifold assembly remain outside the body during a material removal operation. An advancer system may be integrated in the control unit and incorporates slip seals for the drive shaft, aspiration and/or infusion connections, and additionally incorporates a track system for axially displacing the rotating drive shaft and cutter assembly relative to the control unit. The control unit preferably comprises a base arranged so that the control unit may be stably supported on a work surface or a body surface during material removal operations. The control unit also preferably incorporates control systems for actuating, adjusting and providing system information concerning power, drive shaft rpm, drive shaft axial translation, aspiration, infusion and the like.

The material removal system of the present invention incorporates, or is used in conjunction with, a flexible guidewire that is navigated through one or more lumens in a subject, such as blood vessels, to a desired material removal site. Many suitable guidewires are known in the art and may be used with the material removal system of the present invention. Guidewires having a diameter of from about 0.005 inch to about 0.015 inch and having an atraumatic tip are preferred. The guiding catheter assembly generally houses the cutter assembly drive shaft, incorporating a bearing system for rotating the drive shaft and, in some embodiments, defines a lumen for the aspiration and/or infusion of fluids. The guiding catheter assembly may be fixed to and advanced in concert with the cutter assembly drive shaft, or it may be rotatable and/or translatable independently of the cutter assembly drive shaft. The guiding catheter assembly and the guidewire are introduced into a lumen of a patient, such as the femoral artery, and navigated or guided to the site of the desired material removal operation.

A guidewire brake or clamp is preferably provided in proximity to or integrated with the material removal system to hold the guidewire in a stationary, fixed position during operation of the cutter assembly. Rotation and axial displacement of the guidewire may be prevented using either an automatic or a manual grip. An automatic guidewire braking system may be implemented using a solenoid-activated brake that is automatically actuated to brake during activation of the cutter assembly motor drive. A manual guidewire braking system may be actuated by a manual, over-center clamp, cam and brake shoe assembly or another mechanical device. An interlock system may be incorporated in connection with a manual brake system to prevent actuation of the cutter assembly drive system if the guidewire is not in a clamped, stationary condition.

An aspiration source and collection vessel may be provided as a commercially available evacuated container having a suitable volume. Alternatively, the aspiration source and collection vessel may be provided as a syringe or similar device actuated by a motor, pressurized gas, or the like. The aspiration source may alternatively be provided as a small, electrical vacuum pump with a suitable collection device.

Figure 1B:
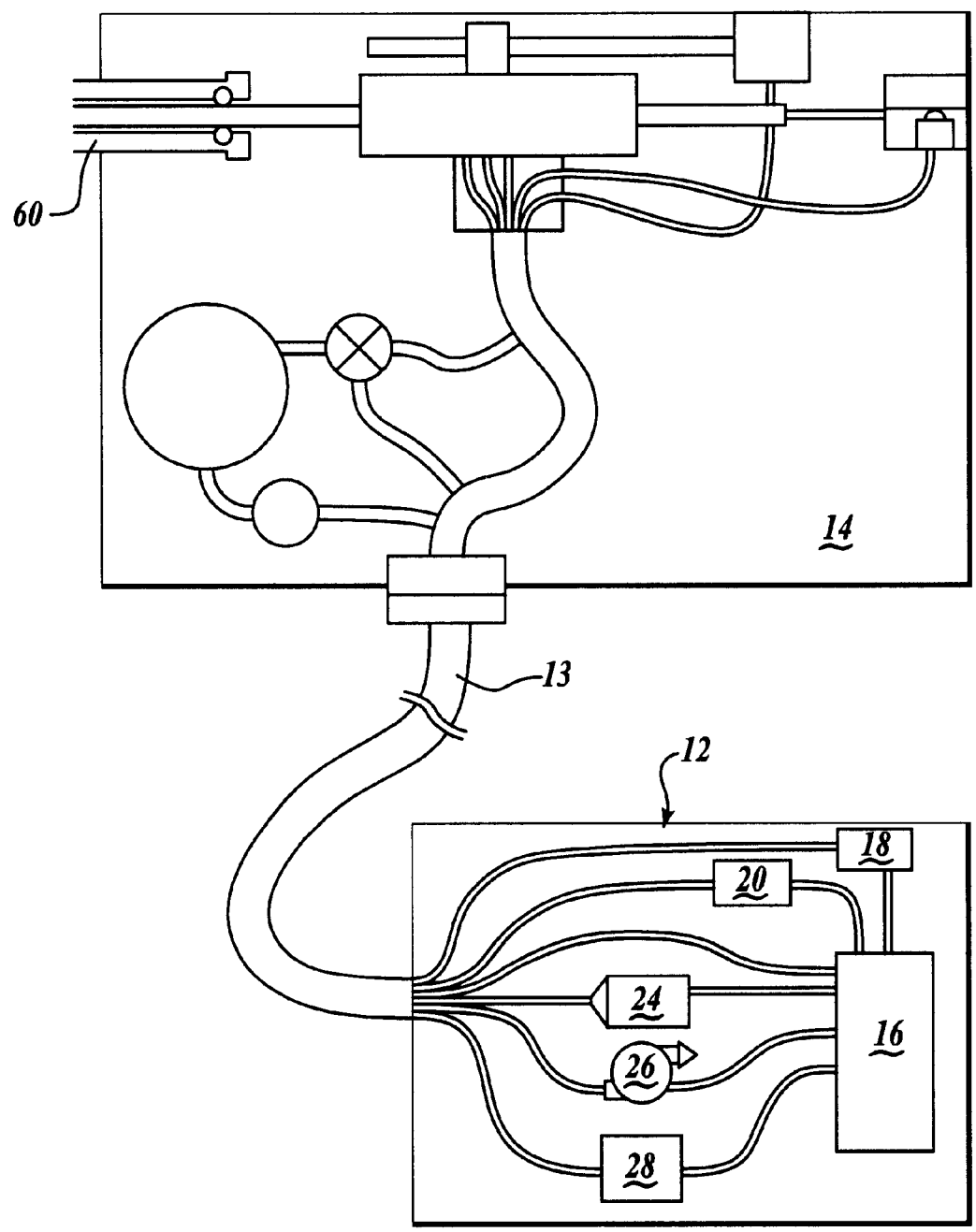
FIG. 1B shows a schematic diagram of a material removal advancer and control system of the present invention illustrating several of the subsystems.

The configuration and construction of the control unit and the manifold assembly may be of various designs, depending on specific desired applications for intralumenal material removal. Suitable designs and configurations are well known in the art. FIGS. 1A and 1B show schematic diagrams of one arrangement, wherein control unit 12 is provided as a separate unit in electrical and operating communication via a flexible cable 13 with advancer unit 14. Advancer unit 14 is configured ergonomically and constructed for placement in proximity to and/or in contact with the patient. In the embodiment illustrated schematically in FIG. 1A, the base of advancer unit 14 is configured to rest stably on the leg of a patient while a material removal operation takes place. Advancer unit 14 may additionally have a work platform providing a level surface for use of the operator and associated medical professionals.

In the embodiment illustrated in FIGS. 1A and 1B, control unit 12 houses a programmable logic controller and power source 16 in operable communication to provide power and to control operation of vacuum control unit 18, cutter assembly advancer unit 20, guidewire brake unit 22, cutter assembly drive system 24, aspiration control unit 26 and temperature control unit 28. As illustrated schematically, control unit 12 may be provided as a separate console and may incorporate various displays for providing information concerning operating conditions and feedback from the material removal site to the operator. According to one embodiment, control unit 12 provides continuously updated output to an operator including such operating parameters such as temperature at the material removal site; cutter assembly rotation rate and/or advance rate; aspiration rate and/or volume; infusion rate and/or volume; and the like. Control unit 12 may additionally provide adjustable controls permitting the operator to control operating parameters of the cutter assembly and material removal operation. Alternatively, adjustable controls and feedback data may be incorporated in advancer unit 14, or a single integrated control and advancer unit may be provided.

Vacuum control unit 18 may comprise, for example, a solenoid operated vacuum valve. Cutter assembly advancer unit 20 may comprise, for example, a stepper motor. Guidewire brake unit 22 may comprise, for example, a solenoid actuated braking device. Cutter assembly drive system 24 for rotating the cutter assembly may be operated using a pneumatic or electric-powered motor. Aspiration control 26 may comprise, for example, a vacuum assist motor/pump. Temperature control monitor 28 may be in operable communication with a temperature probe providing continuous or intermittent feedback relating to the temperature or temperature changes at the site of the material removal operation.

In preferred embodiments of the present invention, a high-speed electric motor supplied by a battery power source is utilized for cutter assembly drive system 24. The motor may be geared and/or separated by a short flexible drive shaft that couples the motor to the cutter assembly drive shaft. The motor may thus be mounted off-axis with respect to the drive shaft. This arrangement also permits translation and advancing of the drive shaft independent of the motor, permitting the motor to remain stationary during material removal operations. In alternative embodiments, the motor assembly and other components, such as the drive shaft and cutting assembly may be axially translatable in the advancer unit, as described in more detail below.

According to preferred embodiments of the material removal system of the present invention, the drive system may be unidirectional and capable of rotating drive shaft 25 in one rotational direction, or it may be selectively bi-directional and capable of rotating drive shaft 25 selectively in both a clockwise and counterclockwise direction. Drive system 24 is also preferably capable of rotating drive shaft 25 at variable speeds ranging from 500 rpm to 150,000 rpm, more preferably from 500 to 60,000 rpm. In an exemplary embodiment of the invention, drive system 24 is a direct current variable speed micro-motor capable of operating at rotational speeds of from 500 rpm to 150,000 rpm. It is understood that a variety of motors may be employed in the system and the range of speeds and capabilities may vary according to the type and site of material removed, and the type of cutter assembly utilized. The present invention also contemplates the use of alternative means of rotating drive shaft 25, such as air-driven turbines, and the like.

A proximal end of drive shaft 25 is operably connected directly, or via a coupler or transmission system, to drive system 24, while a distal end of drive shaft 25 is operably connected, directly or via a coupler, to the cutter assembly mounted to a distal end of drive shaft 25. Drive shaft 25 is preferably a flexible, hollow, helical, torque-transmitting shaft. Hollow, multi-filar metallic drive shafts are known in the art and are suitable for use with the material removal system of the present invention. Multi-filar stainless steel coil drive shafts having a bi- tri- or quad-filar construction are preferred. Coil drive shafts having an inner diameter of from about 0.015 to 0.025 inch and an outer diameter of from about 0.025 to 0.035 inch are preferred for atherectomy applications.

Figure 1C:
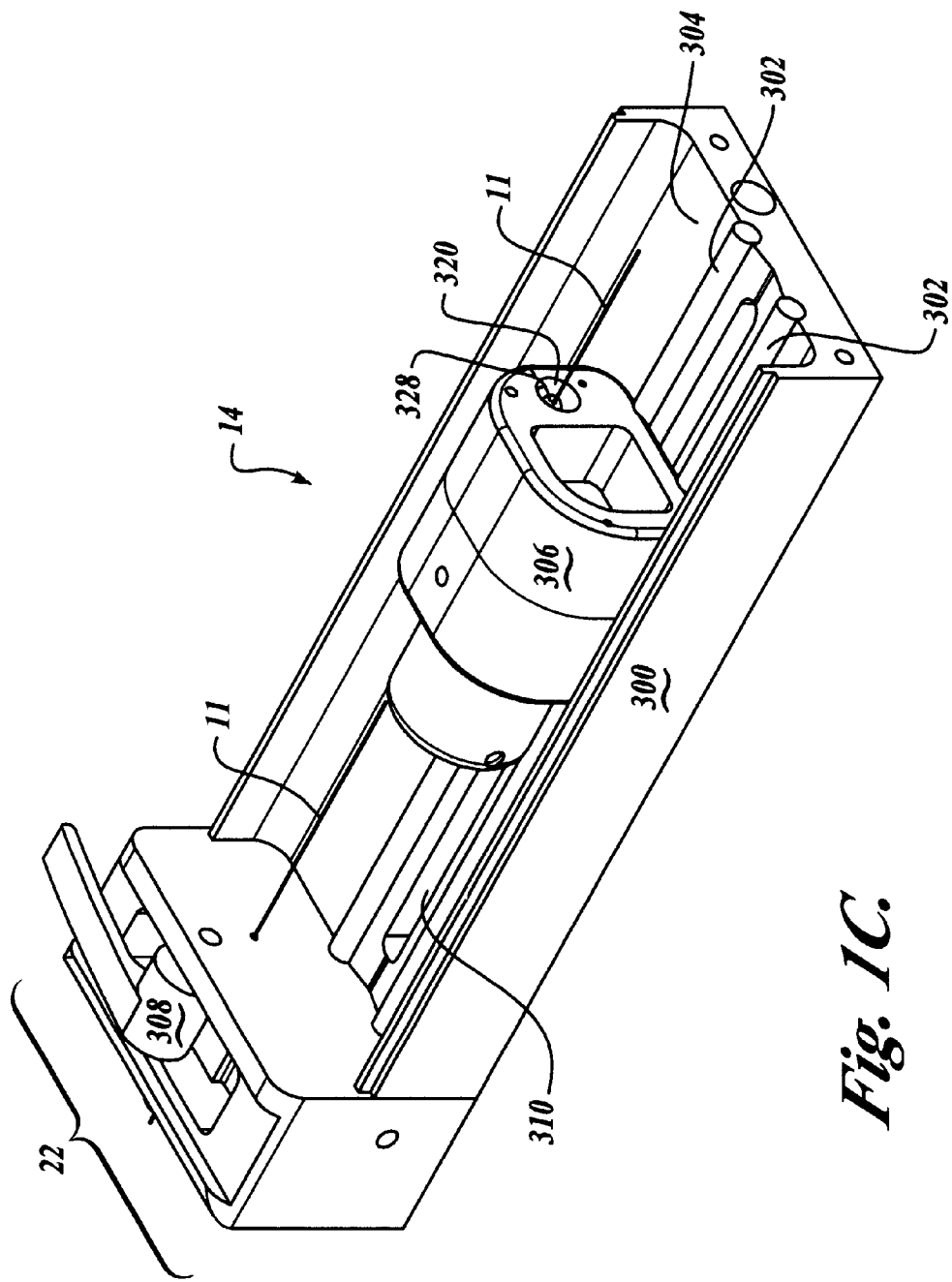
FIG. 1C illustrates one possible embodiment of a material removal tracking unit.

FIG. 1C illustrates a preferred embodiment of an advancer unit 14' for axially translating drive shaft 25 and associated components. Advancer unit 14' is also referred to herein as a "tracking unit." Tracking unit 14' comprises a body 300 having one or more axial translation mechanisms, such as rails 302 running along the longitudinal axis of bed 304 on which rides a motor assembly 306. Alternative embodiments of the present invention may employ any conventional axial translation mechanisms including rails, slots, tracks, wheels, and the like. Motor assembly 306 engages rails to permit controllable axial translation in either an antegrade and retrograde direction, which in turn facilitates axial translation of expandable cutter assembly and associated components. Motor assembly 306 may house several components and assemblies, such as, but not limited to one or motors, drive shafts, gear drives and the like. In preferred embodiments, one or more drainage apertures and/or reservoirs 310 are provided to facilitate removal of aspirate and other fluids and materials. A guide wire brake system 22' is fixedly connected to the proximal end of body 300 and serves to releasably restrict axial and rotational movement guide wire 11. In this particular embodiment, a movement-restricting mechanism 308, such as a cam-lever and brake shoe(s) assembly, is housed within guide wire brake system 22'. Embodiments of the present invention may incorporate any conventional movement-restriction mechanism or mechanisms which serve to controllably limit axial and rotational movement of guide wire 11. Tracking unit 14' may further comprise a cover encompassing motor assembly 306 and bed 304. In addition, a locking mechanism may be provided to tracking unit 14' that controllably restricts axial movement of motor assembly 306. Any conventional locking mechanism may be employed in the present invention, such as, but not limited to a system whereby a restrictive force is exerted from tracking unit cover to motor assembly 306. For example, an element may extend from the top face of motor assembly through a longitudinal slot in the tracking unit cover which may be held in tight association with the cover by a clamping device, such as a threaded knob. Of course, various embodiments of the present invention envision may include any of a wide variety of conventional locking mechanisms.

Figure 1D:
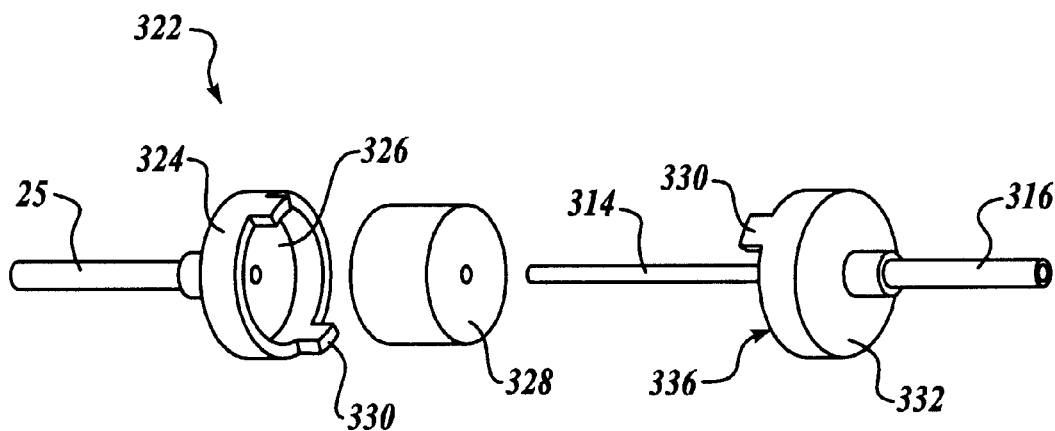
FIG. 1D shows one possible embodiment of a magnetic coupler assembly.
Figure 1E:
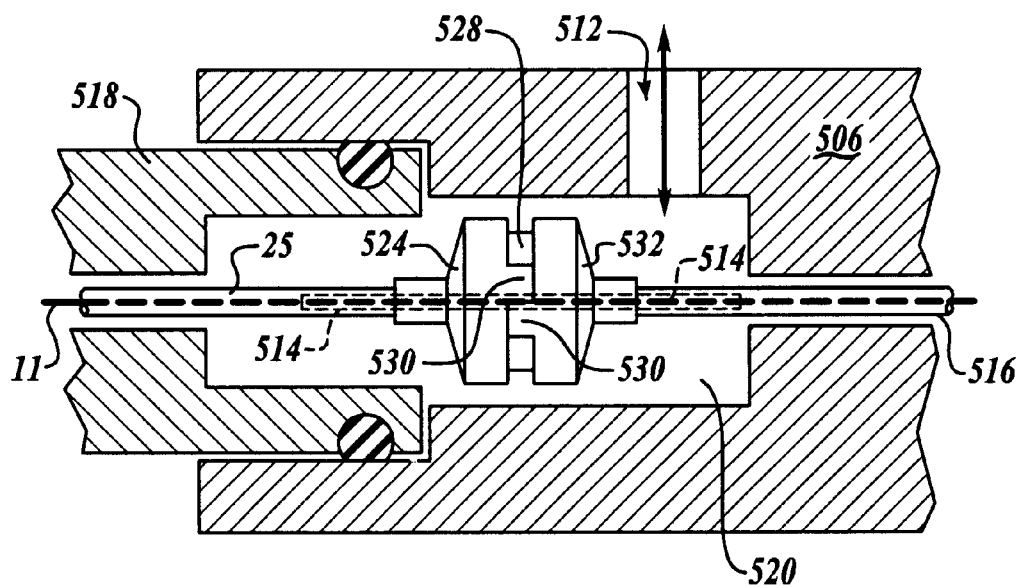
FIG. 1E depicts one embodiment of a magnetic coupling system in association with a drive train, drive shaft and motor housing.

Guide wire 11 passes through brake system 22' into motor assembly 306 and exits from a coupler recess 320 formed in distal face of motor assembly 306. Housed within coupler recess 320 is a drive shaft to drive train coupling assembly. In preferred embodiments, a magnetic coupler 322 is provided, as shown in FIGS. 1D and 1E. In this particular embodiment, magnetic coupler 322 comprises a drive shaft connector 324 having a first magnet recess 326 for receiving and magnetically engaging one or more magnets 328, as well as a plurality of anti-slip cogs 330. A complementary drive train connector 332, also having a plurality of anti-slip cogs 330, has one or more magnets 328 fixedly connected to drive train connector recess 336. Drive train connector 332 further comprises a guide tube 314, which passes through complementary central apertures of drive train connector 332 and magnet 328 to extend beyond the distal face of magnet 328. Guide tube 314 serves to align and guide drive shaft connector 330 to properly seat and releasably engage magnet 328 of drive train connector 332. Drive shaft connector 324 is provided with a central aperture for receiving guide tube 314, thereby aligning drive shaft connector 324 with drive train connector 332 and maintaining a concentric arrangement.

FIG. 1E illustrates magnetic coupler assembly 322 in the context of coupler recess 320 of motor assembly housing 306. In this depiction, drive shaft connector 324 has releasably engaged drive train connector 332 by passing guide tube 314 through central aperture of drive shaft connector 324 and magnetically adhering to magnet 328 such that anti-slip cogs 330 are offset and engaged. In operation, rotational movement is imparted to drive train 316 by any conventional drive system whereby drive train connector transfers rotational movement to drive shaft connector 324 by engaging complementary anti-slip cogs 330 on each connector. Drive shaft 25 is fixedly connected to drive shaft connector 324 by any conventional methods, such as welding laser welding, soldering, brazing, adhesive bonds and the like. Rotational movement imparted to magnetic coupler assembly 322 by drive train 316 is effectively transferred to drive shaft 25 and expandable cutting assembly. Magnetic coupler 322 is designed to accommodate guide wire 11. Drive train 316 and all distal components are provided with a central aperture to receive guide wire 11, thereby permitting free axial translation of guide wire through the entire system.

Preferred embodiments may include additional features, such as an aspiration/infusion portal 312, by which aspirate may be removed from and infusion materials may be introduced into various catheter systems. Additionally, embodiments of the present invention may employ a plurality of connecting devices of any conventional design and type to facilitate connecting various catheters and sheaths to various components. A wide variety of "quick-connect" devices are well known in the art and may be used throughout the present invention. Such connecting devices may provide a fluid-tight seal. For example, FIG. 1E depicts a connector 318 forming a fluid-tight seal with coupler recess 320 of motor assembly housing 306, which may be further connected to one or more catheters and/or sheaths of the present invention. This design, and any similar variations, enables the operator to quickly and efficiently switch components of the present invention.

A conduit for aspirate may be integrated into the drive shaft by bonding or shrinking a polymer onto the outer and/or inner surface(s) of the coil drive shaft. DuPont's TEFLON® brand polytetrafluoroethylene is an especially preferred polymer for sealing the drive shaft. For many applications of the material removal system of the present invention, utilization of a non-compressible multi-filar metallic coil drive shaft without an integrated aspirate conduit is preferred, with one or more conduit(s) for aspiration and/or infusion being provided internally or externally coaxial with the drive shaft, or as a bi-axial conduit. Assemblies of this type may be constructed from materials that provide enhanced system flexibility and guidance properties.

Figure 15:
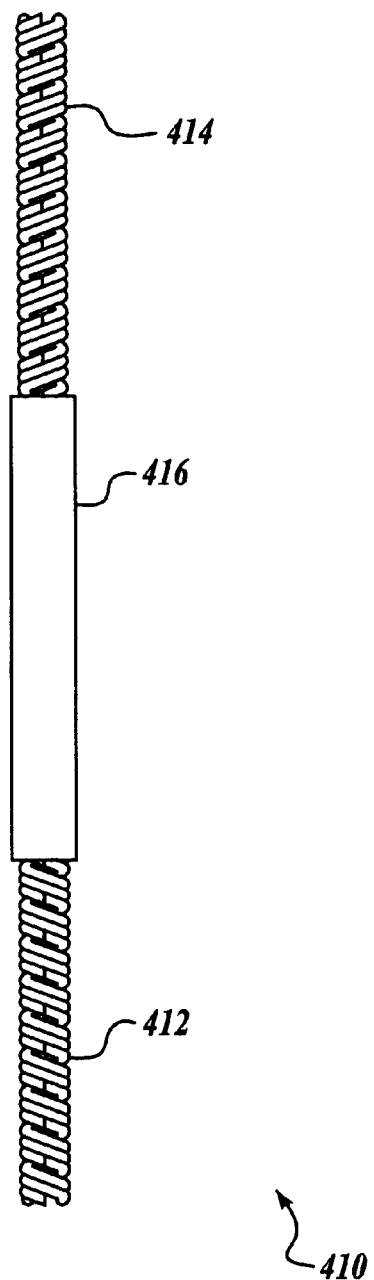
FIG. 15 shows a drive shaft of the present invention having right-lay and left-lay helical configurations.

In one preferred embodiment of the present invention, the flexible, hollow drive shaft comprises a self-dampening drive shaft having a "multi-helical" configuration, herein referred to as a multi-helical drive shaft or simply as a drive shaft. In practice, helically wound drive shafts tend to experience "darting" upon sudden rotational movement at high rpm. Depending upon the "lay" of the helical structure and the direction of rotation, helical drive shafts undergo transitory expansion or contraction caused by unwinding or cinching of the helical structure in response to the applied torque, resulting in axial displacement of the cutting device. This undesirable axial displacement of the drive shaft poses a potential hazard to the patient and added complications for the operator. As shown in FIG. 15, multi-helical drive shaft 410 has adjoining sections of "left-lay" and "right-lay" helical configurations 412 and 414, respectively, each section of substantially equivalent length. The "left-lay" and "right-lay" sections 412 and 414 may be arranged along the longitudinal axis of multi-helical drive shaft 410 in any operable configuration, such as, but not limited to, essentially half the drive shaft length being one continuous length of one lay and the remaining substantially equal length being one continuous lengthy of opposite lay; or a plurality of alternating sections of opposite lay sections of any length, such that, in sum, the multi-helical drive shaft is substantially half left-lay and half right-lay.

A multi-helical drive shaft having adjoining lengths of oppositely wound helical coils dampens the movement of adjoining, counterpart section(s). For example, upon counterclockwise rotation, left-lay coiled section(s) of the drive tend to unwind, causing axial displacement in the distal direction, while the right-lay section(s) of the drive shaft will tend to contract, causing axial displacement in the proximal direction. The combined opposing forces and actions effectively cancel the axial movement of each respective section, resulting in negligible axial movement of the distal expandable cutter. The multihelical drive shaft may have any number of opposite-lay sections, provided that opposite-lay sections are properly matched to effectively dampen the axial movement. The opposite lay coils 412 and 414 may be joined together directly, or, as shown in FIG. 15, by means of a fixed connection to a conventional coupler 416 interposed between the coils. Such fixed connections may be provided, for example, by welding, soldering, brazing, adhesives and the like.

The guiding catheter assembly provides a sheath that houses the drive shaft and is inserted in a patient, over a guidewire, and guided to a material removal site. The guiding catheter is constructed from a material that is flexible, biocompatible, and impermeable to fluids. The guiding catheter assembly may comprise a plurality of coaxially arranged sheaths and catheters housing rotatable drive shaft 25 and guidewire 11. In a simplified embodiment, a flexible guiding catheter 40 is sealed at a proximal end to control unit 12 and may be sealed, at a distal end, to the cutter assembly. Intermediate catheter systems, manifolds, and the like, may be interposed at various locations along the length of the guiding catheter. The guiding catheter, or one or more internal sheath(s), is preferably sealed to provide one or more sealed lumen(s) for aspiration and/or infusion of fluids.

The dimensions and preferred materials of construction for guiding catheters are well known in the art. The desired dimensions of the guiding catheter depend upon the material removal application and site, and the configuration and placement of aspiration and/or infusion conduits. The outer diameter of the guiding catheter is smaller than the inner diameter of all anatomical lumens through which it is intended to be guided, and the inner diameter of the guiding catheter is large enough to accommodate internal components, as described in greater detail below. A proximal end of the guiding catheter is mounted through a manifold fluid seal located at a distal end of the manifold. The manifold fluid seal may be of any conventional design and provides a fluid-tight seal between the lumen of the manifold, the exterior environment, and the guiding catheter. A distal end of the guiding catheter is preferably in proximity to and/or sealed to a proximal portion of cutter assembly 42. According to one embodiment, the guiding catheter is sealed at a proximal end to the manifold and at a distal end to the cutter assembly. In this embodiment, a sealed lumen 41 is provided between the inner surface of guiding catheter 40 and drive shaft 25 that may be employed as a conduit for aspiration and/or infusion of liquids.

According to another embodiment, a hollow primary sheath is arranged, generally coaxially, within the lumen of guiding catheter 40. The outer diameter of the primary sheath is smaller than the inner diameter of guiding catheter 40, forming a lumen between the outer wall of the primary sheath and the inner wall of the guiding catheter. A suitable primary sheath may be constructed from a suitable, flexible, biocompatible material. A proximal end of the primary sheath extends into the lumen of the manifold, and a distal end of the primary sheath is operably connected to the cutter assembly, or a fixture in communication with the cutter assembly. Various embodiments of the present invention may employ any number of coaxially arranged catheters and/or sheaths to provide one or more conduits for working components, such as a drive shaft, aspirate and infusion materials, as well as serve as intralumenal delivery vehicles for the expandable cutting assembly.

As described in greater detail below, a preferred material removal system of the present invention has the ability to remove material from the interior of a lumen, such as a blood vessel or gastrointestinal lumen, in a two-step process using an expandable cutter assembly. The expandable cutter assembly preferably has a dual cutter configuration employing a distal, fixed diameter cutter and a proximal, adjustable diameter cutter. In preferred methods, the dual cutter assembly is rotated and advanced to remove occlusive material in an initial "pilot pass" in which the distal, fixed diameter cutter is the primary cutter, and the proximal, expandable cutter is in a smaller diameter condition. Following one or more pilot passes, the proximal, adjustable diameter cutter is adjusted to a larger diameter condition and the dual cutter assembly is advanced so that the adjustable diameter cutter, in its expanded condition, cuts an even larger volume of occlusive material. Debris and fluids are preferably removed from the site by aspiration. Following removal of desired materials, the proximal, adjustable diameter cutter is adjusted to a smaller diameter condition and the cutter assembly is withdrawn from the site. This method, using the material removal system of the present invention, obviates the need for the operator to remove and replace, or interchange, cutter assemblies during a material removal operation to provide cutters having different diameters and material removal capabilities.

Figures 2, 3:
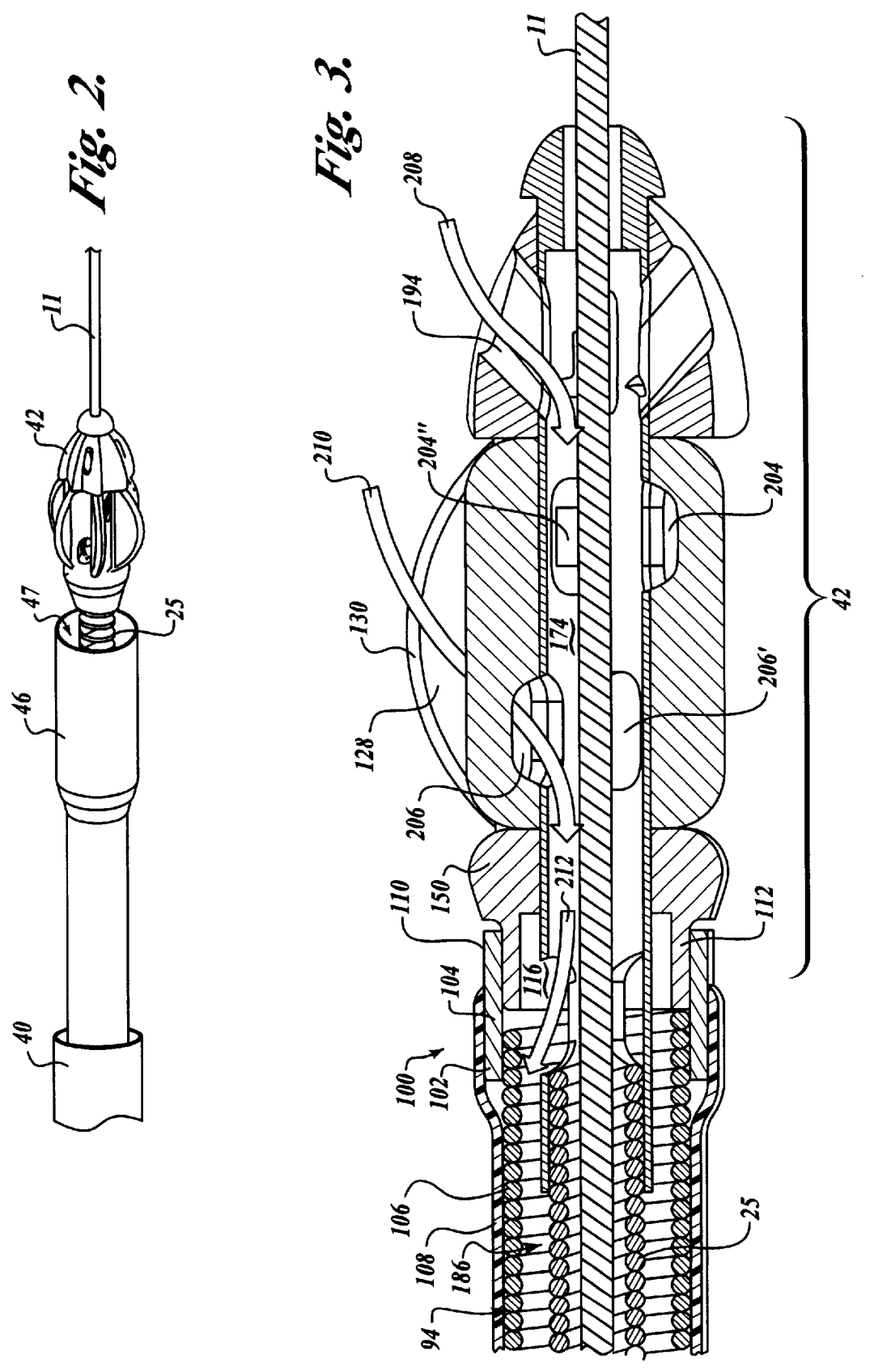

An enlarged cutter assembly housing 46 may be provided at distal end of guiding catheter 40 or primary sheath. In one embodiment, the cutter assembly housing 46 may be provided as a continuous, enlarged section of guiding catheter 40 or a primary sheath that accommodates cutter assembly 42. As shown in FIG. 2, for example, the hollow interior of cutter housing 46 defines an interior space 47 in which the cutter assembly 42 resides when axially retracted in a proximal direction. Interior space 47 of expandable cutter housing 46 is continuous with the lumen of a primary sheath or the lumen of guiding catheter 40, creating a conduit for the flow of various fluids during aspiration and/or infusion. In another embodiment, the distal end of a primary sheath or the guiding catheter is operably connected to a flared coupling that serves as a cutter assembly housing.

Figure 4:
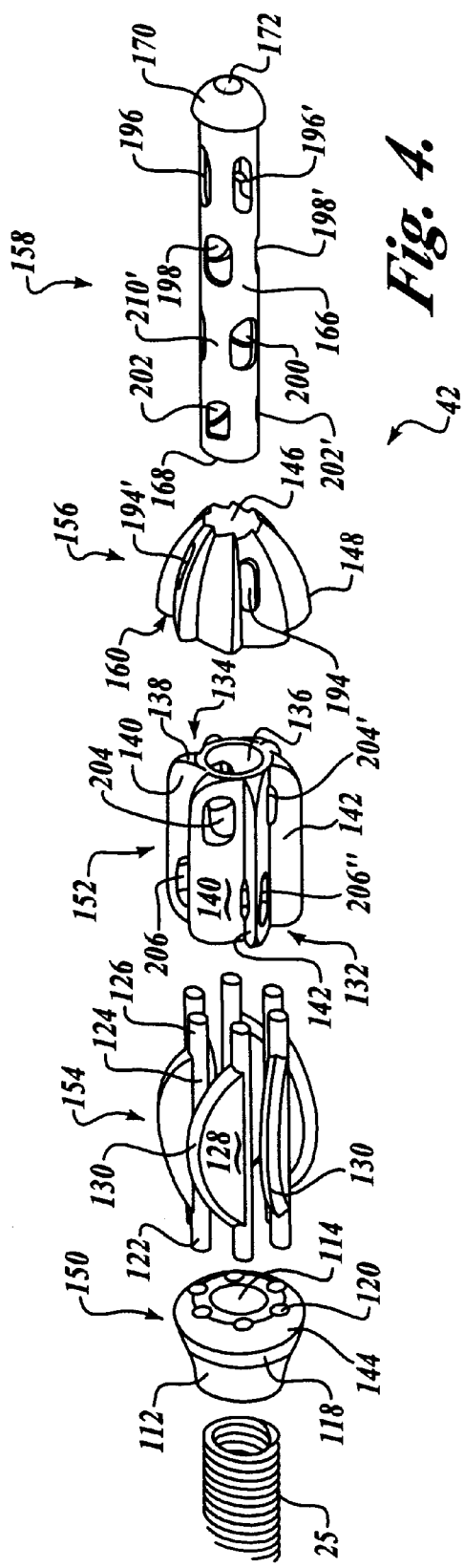
FIG. 4 shows an enlarged, exploded perspective view of one embodiment of an expandable cutter assembly of the present invention.

As illustrated in FIGS. 3 and 4, a distal end of drive shaft 25 is fixedly connected to expandable cutting assembly 42. In general, cutter assembly 42, as illustrated in FIGS. 3 and 4, is a dual cutter assembly comprising a proximal bushing 150, an adjustable cutter housing a central block 152 and a plurality of cutting members 154, a fixed diameter distal burr 156 and an assembly tube 158. Preferred materials for the components of the expandable cutter assembly 42 include metals, metal alloys and ceramics, such as but not limited to, various types of stainless steels, such as series 300 and/or 400, vanadium steel, nickel-titanium, titanium, titanium-containing metals and oxide ceramics. Expandable cutter assemblies of the present invention and the accompanying drives, catheter assemblies, etc., may be constructed having various sizes and configurations to accommodate different material removal applications. For example, expandable cutter assemblies may be provided in several diameters, ranging from less than 2 mm to 5 mm or more. In particular, the expandable cutter assembly may have a contracted diameter/expanded diameter of 2.25 mm/2.75 mm, 2 mm/2.75 mm and/or 1.5 mm/2.0 mm, or the like.

In the specific embodiment illustrated in FIG. 3, a hollow flexible conduit catheter 94 is coaxially disposed within the lumen of a primary sheath or guiding catheter. Conduit catheter 94 may be constructed from plastic such as polyvinyl chloride (PVC), TEFLON® brand polytetrafluoroethylene, Nylon or another polymer, or from a helical metal spring wire encased in a suitable polymer to provide a sealed conduit. Conduit catheter 94 provides a conduit for aspiration and therefore must have sufficient structural integrity to withstand the internal vacuum pressure during aspiration, as well as sufficient flexibility to permit guidance and axial movement of the expandable cutting assembly in an atralimatic manner. In preferred embodiments, conduit catheter 94 is a coiled metallic catheter 106 having a tightly associated flexible outer sheath 108, such as a TEFLON® sheath which has been "shrink-wrapped" onto the outer surface of the coiled metallic catheter. The present invention comprehends other suitable materials for encasing the stainless steel coiled catheter, such as any flexible, biocompatible plastic or synthetic material. A sheathing layer may also be applied using techniques other than heat shrinking, such as, but not limited to, plastic extrusion techniques. The outer diameter of conduit catheter 94 is smaller than the inner diameter of guiding catheter 40 or primary sheath. According to preferred embodiments, conduit catheter 94 has an outer diameter of from about 0.045 to 0.060 inch and an inner diameter of from about 0.035 to 0.050 inch. The lumen formed between conduit catheter 94 and drive shaft 25 serves as a conduit for fluids and particulates during aspiration and perfusion.

A distal end 100 of conduit catheter 94 is fixedly connected to a proximal section 102 of a first slip seal/bearing assembly 104. Slip seal/bearing assembly 104 is a mechanism for coupling conduit catheter 94 to expandable cutter assembly 42, while permitting free rotation of cutter assembly 42 around a central axis and forming a fluid-tight junction between conduit catheter 94 and cutter assembly 42. Outer sheath 108 of conduit catheter 94 extends to partially cover the outer wall of the proximal section of slip seal/bearing assembly 104. A distal section 110 of first slip seal/bearing assembly 104 is in close association with the collar section 112 of proximal bushing 150, thereby forming the slip seal/bearing junction 104. Collar section 112 of proximal bushing 150 is continuous with body section 118 of proximal bushing 150. Proximal bushing. 150 has an axially-aligned central aperture 114, which enlarges at collar section 112 to form a proximal bushing conduit 116. The axially-aligned central aperture 114 receives assembly tube 158. Proximal bushing 150 also possesses a first series of receiving apertures 120 radially arranged around central aperture 114 for receiving proximal end 122 of rod section 124 of cutting members 154. The present invention contemplates proximal bushings having various configurations, such as but not limited to, a bushing having raised ridges that act as a cutting or grinding burr for removing material when the cutter assembly is operated in a retrograde axial direction.

Figure 5:
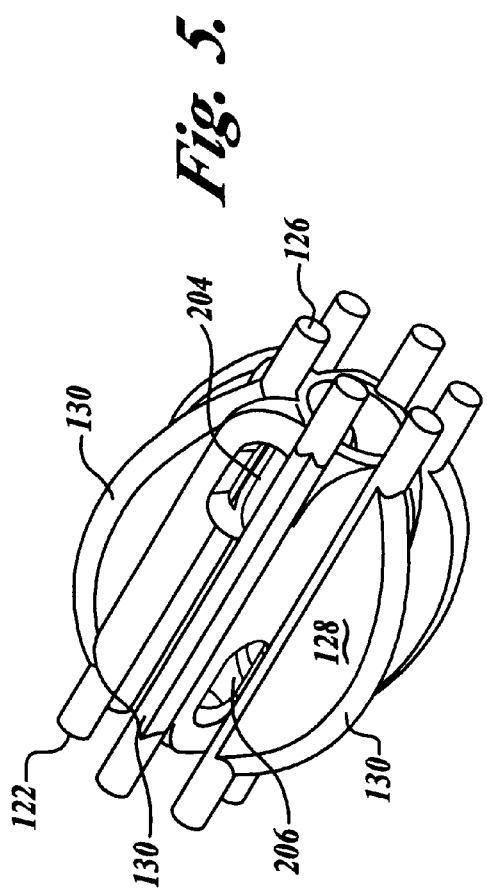
FIG. 5 shows an enlarged, side perspective view of one embodiment of the cutting members in association with the central block of an expandable cutter assembly of the present invention.
Figure 6A:
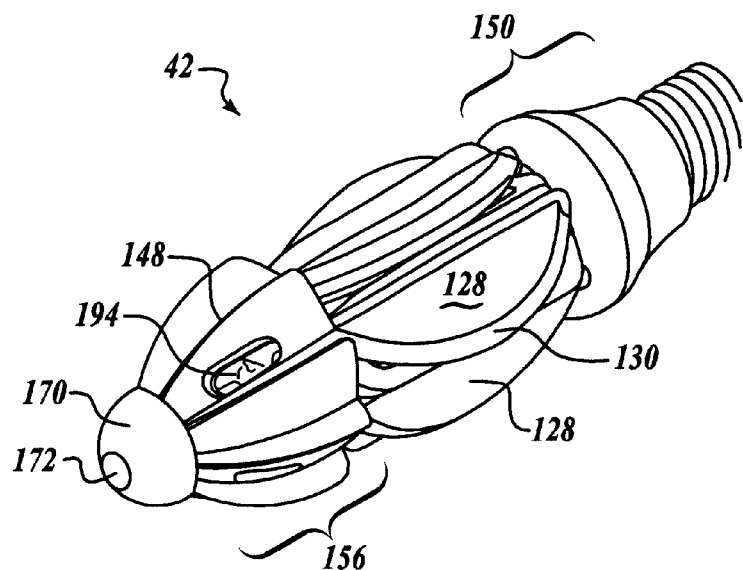
FIG. 6A illustrates an enlarged, perspective view of one embodiment of a dual cutter assembly of the present invention with the cutter assembly in a contracted configuration.
Figure 6B:
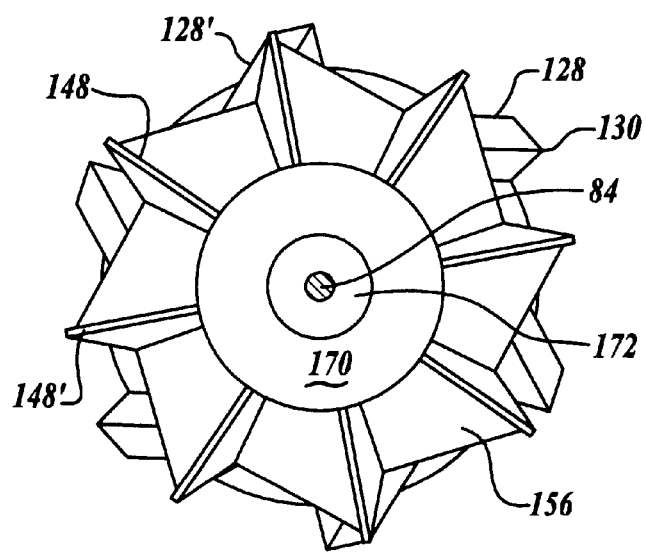
FIG. 6B illustrates an enlarged, front view of one embodiment of the dual cutter assembly of FIG. 6A with the cutter assembly in a contracted configuration.

As shown in FIGS. 4 and 5, cutting members 154 comprise a rod section 124, having a proximal end 122 and a distal end 126. Along the middle portion of each rod section, a blade 128 having a beveled edge 130 for cutting is mounted. It is understood that the beveled edge 130 of the blade(s) may be of different configuration to facilitate the removal of occlusive material. Rod sections 124 of cutting members 154 are seated onto central block 152.

Central block 152 supports a plurality of cutting members 154 and provides a central lumen 136 for receiving assembly tube 158. Central block 152, having a proximal 132 and a distal 134 end, also serves as a control mechanism for the axial rotation of cutting members 154, which is explained in detail below. Central block 152 preferably incorporates a plurality of raised spines 138 tangentially arranged around its central axis. Raised spines 138 have a support face 140 and a stop face 142. The junction between raised spines 138 forms a seat for receiving rod sections 124 of cutting members 154. A proximal end 132 of central block 152 may be permanently fixed to a distal face 144 of proximal bushing 150 using any conventional means, including but not limited to, welds of all types, mechanical attachments and adhesives.

In preferred embodiments of the present invention, and as depicted in the accompanying drawings, six cutting members 154 are mounted on a central block configured to support six cutting members. Cutting members 154 are seated in the junctions of raised spines 138 of central block 152, with the blade section 128 of each respective cutting member 154 contacting the support face 140 of the corresponding raised spine 138 of central block 152. The distal end 126 of each rod section 124 of cutting members 154 extends distally beyond the distal end 134 of central block 152 to engage the proximal face 160 of a distal cutter 156 having a fixed diameter.

As shown in FIGS. 2, 3, 4, 6 and 7, the fixed diameter distal cutter 156 typically has a frusto-conical cross-sectional configuration and a series of raised cutting flutes 148. The raised cutting flutes 148 of distal cutter 156 operate according to the principle of differential cutting and operate to cut, scrape or grind occlusive material, without damaging other tissues, such as internal blood vessel surfaces. In fact, cutting edges of both distal cutter and cutting members 154, according to the principle of differential cutting, preferentially remove occlusive material while being atraumatic to the more resilient vessel walls. In preferred embodiments, proximal and distal portions of cutting flutes 148 are chamfered to render them atraumatic. It is understood that the distal fixed diameter cutter may be of any suitable configuration, and numerous fixed diameter cutter configurations are known in the art. The dimensions of the distal cutter vary depending upon the particular application and embodiment but, for intravascular applications, the largest outer diameter of the distal, fixed diameter cutter is generally in the range of 1.5 mm to 2.5 mm.

Distal cutter 156 is provided with a central aperture 146, which defines a surface for mounting assembly tube 158 and receiving the guidewire. A second series of receiving apertures 164 is present in proximal face 160 of distal cutter 156. Receiving apertures 164 are radially arranged around the central lumen, and complementary to the first series of receiving apertures 120 located on distal face 144 of proximal bushing 150. Receiving apertures 164 receive distal end(s) 126 of rod sections 124 of cutting members 154. In certain embodiments of the present invention, the distal cutter may be fixedly joined by a connection means to the central block. This permanent, fixed connection may be achieved by any conventional means, such as a weld, preferably a laser-weld, soldering, brazing or an adhesive bond between the distal end 134 of central block 152 and proximal face 160 of distal cutter 156.

Assembly tube 158 serves as a connecting means for the cutter assembly 42, as well as a bore for receiving guidewire 11 and a conduit for fluids and debris during aspiration and/or infusion. Assembly tube 158 comprises a body section 166, a proximal end 168 and a distal flanged cap section 170 having a central aperture 172 defining guidance passage 174. A proximal end 168 of assembly tube 158 traverses central aperture 146 of distal cutter 156, and central lumen 136 of central block 152, and central aperture 144 of proximal bushing 150 to fixedly connect with the distal end of drive shaft 25. Distal cutter 156, central block 152 and proximal bushing 150 may be fixedly joined to the assembly tube by any conventional connection means, such as but not limited, to welds, adhesives and mechanical connection means, such as compression fitting. The components of the cutter assembly 42 are drawn in and held in tight association by the distal flanged cap section 170 of assembly tube 158.

The present invention has additional features which permit the aspiration of fluids and small particulates from the vessel lumen, as well as perfusion of liquids, such as physiologically balanced salt solutions, diagnostic or therapeutic substances, and/or contrast media into the intralumenal space in proximity to a material removal site. In general, the inventive device has a primary aspiration means through the primary sheath 60, and a secondary aspiration means through a plurality of ports in cutter assembly 42 and lumen 186 formed between flexible conduit catheter 94 and drive shaft 25, which, in some embodiments, is continuous with lumenal space of primary sheath 60. Proximal end of primary sheath 60 is operably connected to a vacuum control unit 18 and may incorporate one or more flow-regulation systems, such as valves, seals, manifolds and the like. Upon actuation of the vacuum assembly and opening of the flow-regulation means, a vacuum is created in the lumen formed by primary sheath that draws fluids and particulates from the material removal site and deposits fluids and associated debris in an aspirate collection means.

A secondary aspiration and perfusion system is provided using a plurality of ports in cutter assembly 42 to draw fluids and particulate debris through lumen 174 of assembly tube 158, providing a conduit which is continuous with lumen 186 of flexible conduit catheter 94 and a lumen of a primary sheath. As illustrated in FIGS. 2–7, cutter assembly 42 is provided with a plurality of ports in assemble tube 158, fixed diameter distal cutter 156 and central block 152. Ports. 194, 194', etc., in distal cutter 156 communicate with assembly tube ports 196, 196', etc. In preferred embodiments, distal cutter ports 194, 194', etc. are interspaced circumferentially around the distal cutter 156. Central block 152 has a first plurality of circumferentially interspaced ports 204, 204', etc., in the distal portion, and a second plurality of circumferentially interspaced block ports 206, 206' etc., in the proximal portion, which are arranged in a staggered configuration. The first plurality of ports 204, 204', etc. define a lumen that is in alignment and continuous with the second group of assembly tube ports 198, 198' etc., and the second plurality of ports 206, 206' etc. define a lumen that is in alignment and continuous with the third group of assembly tube ports 200, 200' etc., such that under vacuum conditions, fluid and particulates flow through cutter ports 194, 194' etc., central block ports 204, 204' and 206, 206' etc. as shown by arrow 208 and 210, respectively. Fluid and particulates continue to flow through assembly tube lumen 174 to a third group of assembly tube ports 202, 202' etc., to lumen 186 of conduit catheter 94, as shown by arrow 212. The infusion of fluids may be provided by switching to an infusion source and reservoir, and reversing flow so that fluid flows through cutter assembly 42 in a direction opposite that of directional arrows 208 and 210.

Operationally, the intralumenal material removal system is introduced into the body by way of a lumen, such as a blood vessel, using techniques that are well known in the art. Typically, an access sheath is employed to access the desired vessel at the point of introduction. Through an installed access sheath, the guiding catheter, which houses the guidewire 11, cutter assembly 42 and other associated components and serves as a delivery vehicle for those components, is navigated and advanced to the desired site of material removal. In general, the guidewire brake 22 is released and distal end of guiding catheter 40 is axially translated to a location proximal to the desired material removal site. Guidance and navigation of guiding catheter and associated cutter assembly may be facilitated by the infusion of fluids, such as contrast media, to monitor the progress of the guiding catheter. The cutter assembly, or sub-components thereof, may be coated with a radiopaque material such as gold, platinum, inks and the like, to render the expandable cutting assembly radioscopically visible and to assist a medical professional in guiding and positioning the cutter assembly relative to an occlusion.

Once the guiding catheter is positioned, the flexible conduit catheter, or other internal catheter, is extended distally to facilitate placement of the cutter assembly near the occlusion. The distal end of cutter assembly 42 is positioned at the proximal boundary of the occlusion, whereupon drive system 24 is actuated and drive shaft 25 and cutter assembly 42 are rotated. In the embodiment illustrated in the accompanying figures, particularly in FIGS. 6A and 6B, cutter assembly 42 is initially rotated in a counter-clockwise direction and advanced so that distal, fixed diameter cutter 156 cuts and abrades the occlusion. Initial rotation of cutter assembly 42, contacting distal cutter 156 with the occlusive material, is capable of removing occlusive material having a cross-sectional area roughly equivalent to the largest outer diameter of distal cutter 156 and diameter central block 152/cutting members 154 assembly in its contracted state. Initial "pilot passes" remove part of the occlusive material and subsequent passes with the cutting assembly in the expanded configuration remove additional material. Of course, alternative embodiments of the present invention may be configured to operate in the opposite rotational direction described above, such that clockwise rotation provides a contracted state and counter-clockwise rotation expands the cutting assembly.

As the distal, fixed diameter cutter assembly is rotated and advanced to remove occlusive material, fluid and debris particulates are aspirated using the primary and secondary aspiration mechanisms described above. It may be desirable to alternate between advancing and retracting cutter assembly 42 to facilitate the aspiration of particulates, especially particulates which are too large to pass through ports 194, 204, 206, etc. in cutter assembly 42. For example, retracting cutter assembly 42 in a retrograde direction (i.e. proximally) within cutter housing 46 of primary sheath 40 during aspiration creates a laminar-like flow, thereby more effectively drawing fluid and particulates into housing 46 and permitting particulates to be further broken down by the grinding action of the rotating cutter assembly within housing 46. Larger particulates may thus be broken down to a size that can be withdrawn, with fluids, through aspiration ports 194, 204, 206, etc.

Figure 7A:
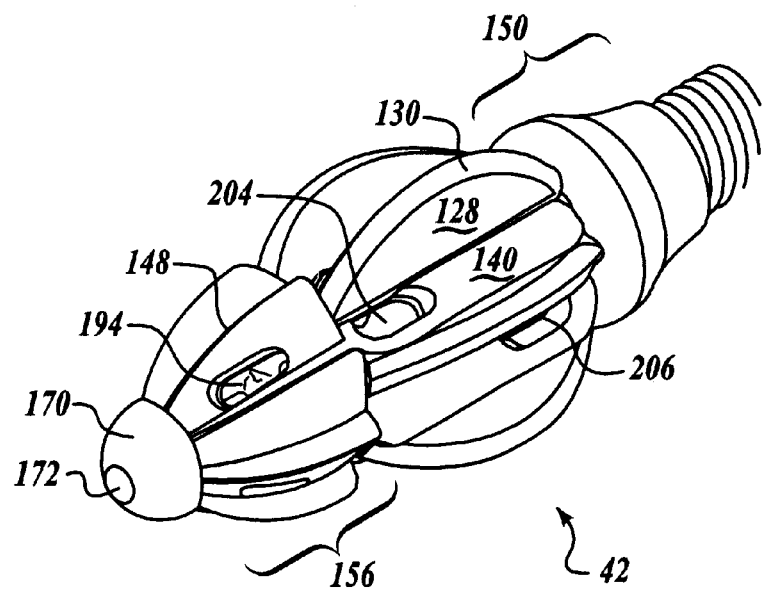
FIG. 7A illustrates an enlarged, perspective view of one embodiment of the dual cutter assembly of FIG. 6A with the cutter assembly in an expanded configuration.
Figure 7B:
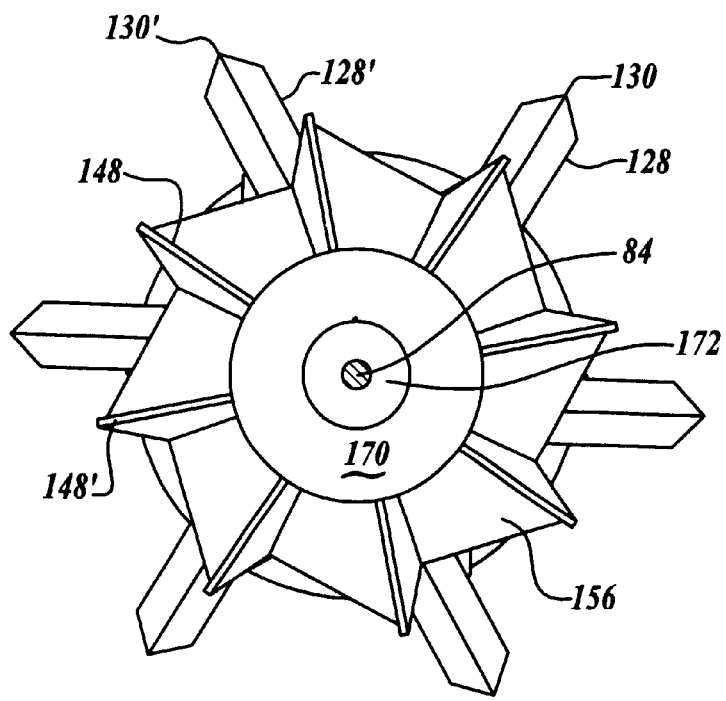
FIG. 7B illustrates an enlarged, front view of one embodiment of the dual cutter assembly of FIG. 7A with the cutter assembly in the expanded configuration.

Once one or more initial pilot-passes are complete, the cutter assembly is retracted in a retrograde direction to the proximal boundary of the occlusion and the direction of rotation of the expandable cutter assembly is reversed. Reversing the direction of rotation from a counter-clockwise direction to a clockwise direction causes cutting members 154 of expandable cutter assembly to open to an expanded configuration, as illustrated in FIGS. 7A and 7B. Specifically, as the expandable cutter assembly 42 is rotated in a clockwise direction, centrifugal forces of rotation combine with hydrodynamic and frictional forces between the surrounding fluid within the lumen and blades 128 of cutting members 154, cause cutting members 154 to rotate around a central axis, as defined by rod sections 124 of cutting members 154. Cutting members 154 rotate freely within the first receiving apertures 120 and second receiving apertures 164 in proximal bushing 150 and distal cutter 156, respectively. Cutting members 154 rotate from a tangential orientation, in which blades 128 are in contact with the respective support faces 140 of raised spines 138 of central block 152 (i.e., the contracted configuration) to a radial orientation in which blades 128 of cutting members 154 are in contact with stop faces 142 of raised spines 138 of central block 152 (i.e., the expanded configuration). Stop faces 142 of raised spines 138 check the rotational movement of the cutting members 154, as well as provide support to blades 128 of cutting members 154 while in the expanded configuration during operation. Movement of the cutting members to the radial configuration increases the overall outer diameter of the cutter assembly. For example, in select embodiments, the outer diameter of the expandable cutter assembly in the contracted configuration is approximately 2 mm, and the cutter assembly is expandable to an outer diameter of approximately 2.75 mm. As previously described, the present invention may be designed in a wide range of sizes to accommodate various applications.

While in the expanded configuration, the expandable cutter assembly is axially translated along guidewire 11 to retrace the pilot-pass made through the occlusion, whereupon beveled edges 130 of cutting members 154 engage the occlusive material, removing a larger volume of occlusive material. As previously described, aspiration is provided throughout the operation of the expandable cutter assembly to effectively remove the particulate debris dislodged during cutting and grinding of the occlusive material.

After sufficient occlusive material has been removed, the expandable cutting assembly is contracted by engaging drive system 24 to rotate cutter assembly 42 in the opposite direction, i.e. for the purpose of this example, in a clockwise direction. The centrifugal, hydrodynamic and frictional forces again act on blades 128 of cutting members 154, causing the cutting members to rotate around a central axis, as defined by rod sections 124 of cutting members 154. Cutting members 154 rotate from a radial orientation, in which blades 128 of cutting members 154 are in contact with stop faces 142 of raised spines 138 of central block 152 (i.e., the expanded configuration) to a tangential position in which blades 128 are in contact with the respective support faces 140 of raised spines 138 of central block 152. Support faces 140 of raised spines 138 stop the rotational movement of the cutting members 154, as well as provide support to blades 128 of cutting members 154 while in the contracted configuration. While in its contracted state, the cutting assembly 42 may be retracted into the primary sheath or guiding catheter for removal from the body or further advanced distally along guidewire 11 to perform additional operations.

FIGS. 8–14B present a preferred embodiment of the present invention. Wherever appropriate, the same reference numbers have been employed to describe the same or similar elements. In general, the dimensions, materials, method of operation and the like used to describe the previous embodiment apply equally to all embodiments presented herein unless stated otherwise.

FIG. 8 depicts an alternative embodiment of the present invention comprising at least one flexible conduit catheter 94' in which drive shaft 25, preferably a multi-helical drive shaft, runs coaxially within its internal lumen. A proximal encasement 340 fixedly connects flexible conduit catheter 94' to a secondary segment of flexible conduit catheter 342, which in turn is fixedly connected to a distal encasement 344. Distal encasement 344 forms a slip-bearing fitting with a proximal cap 346, thereby permitting free rotation of drive shaft 25 and cutting assembly 42' within coiled metallic catheter. As with previous embodiments, cutting assembly 42' comprises a central block 152', a fixed diameter distal cutter 156' and a plurality of cutting members 154'.

Figure 10:
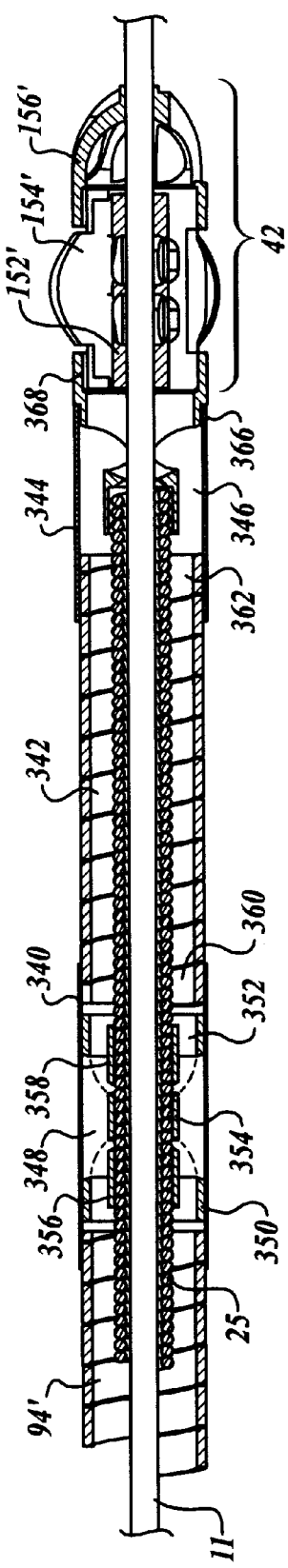
FIG. 10 provides a cross-sectional perspective of an alternative embodiment of the present invention.

As illustrated in FIGS. 9 and 10, drive shaft 25 is provided with retainer assembly or mechanism 338 for interconnecting drive shaft 25 and flexible conduit catheter 94'. Any conventional assemblies or mechanisms may be utilized, such as a retainer 348 having a first end 350 fixedly connected to flexible conduit catheter 94' and a second end 352 fixedly connected to a first end 360 of secondary segment of flexible conduit catheter 342, by any conventional methods, such as by welding, laser-welding, soldering, brazing, adhesive bonds and the like. Retainer 348 works in conjunction with one or more thrust bearings to facilitate cooperative axial translation of drive shaft 25 and flexible conduit catheter 94' in either an antegrade or retrograde direction. A first thrust bearing 356 is fixedly connected to drive shaft 25 proximal to center section of retainer 354, and a second thrust bearing 358 is fixedly connected to drive shaft 25 distal to center section of retainer 354 in such a manner as to bring first 356 and second 358 thrust bearings in close or tight association with center section 354 of retainer 348. Drive shaft 25 freely rotates within central aperture of retainer 348. Retainer assembly may be enveloped by some tubular sheath, such as proximal encasement 340 to add additional strength and provide a relatively smooth profile to flexible conduit catheter 94'.

Notably, retainer assembly 338 and proximal encasement 340 are located an operable distance from cutting assembly 42'. "Operable distance," as used herein, is defined as a distance which permits secondary segment of flexible conduit catheter 342 and associated cutting assembly 42' to retain sufficient flexibility to effectively maneuver within intralumenal spaces, particularly along curved, arched and/or branched sections of lumenal bodies. The distance between retainer assembly 338/proximal encasement 340 and distal cutting assembly 42' may be less than 1 cm to over 20 cm.

Cutting assembly 42' is fixedly connected to drive shaft 25 while permitting free rotation within flexible conduit catheter 94'. Drive shaft 25 is fixedly connected to a proximal cap 346, which has a distal flange section 366 fixedly connected central block 152'. This arrangement transfers rotational movement from drive shaft 25 to cutting assembly 42'. Proximal cap 346 is provided with a central aperture for receiving guide wire 11, and a number of cut-away sections to create one or more accesses continuous with the lumenal space within all sections of flexible conduit catheter 342, 94'. This lumenal space serves as a conduit for aspiration and infusion materials and is continuous with the various ports of cutting assembly 42'. A slip seal/bearing assembly 368 is created at the connection between distal encasement and flange section of proximal cap 366 thereby permitting free rotation of drive shaft 25, proximal cap 346 and cutting assembly 42' within flexible conduit catheter 94', 342 without imparting rotational movement to flexible conduit catheter 94', 342, which minimizes unnecessary trauma to the surrounding tissues.

Figure 11:
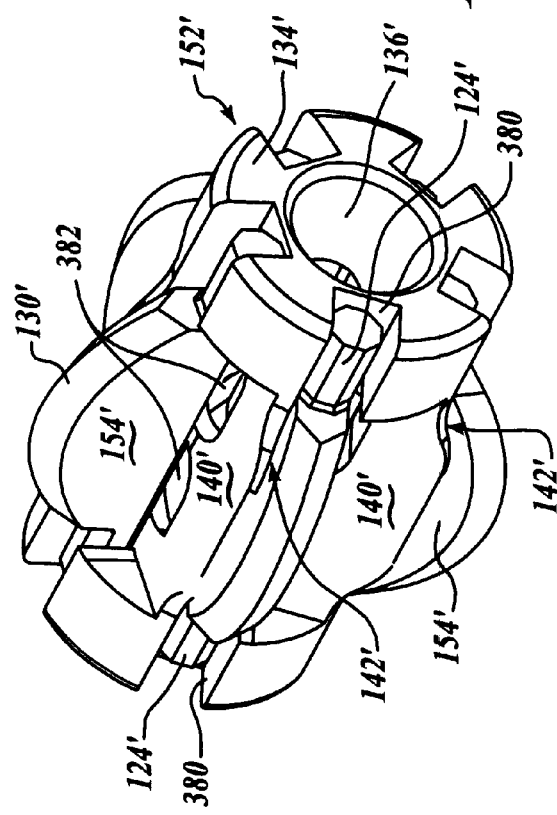
FIG. 11 shows an alternative embodiment of a expandable cutter highlighting the central block and cutting members assembly.
Figure 12A:
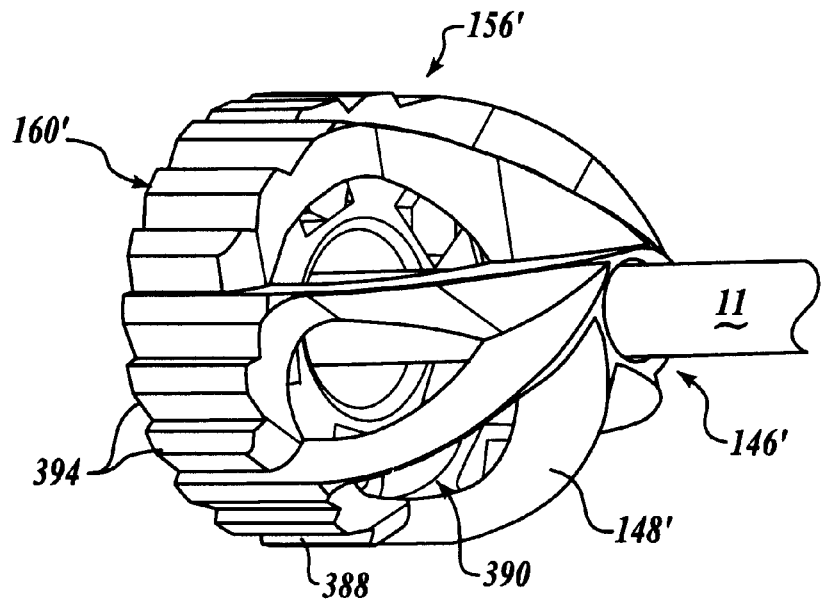
FIG. 12A illustrates a side view of another embodiment of a fixed diameter distal cutter.
Figure 12B:
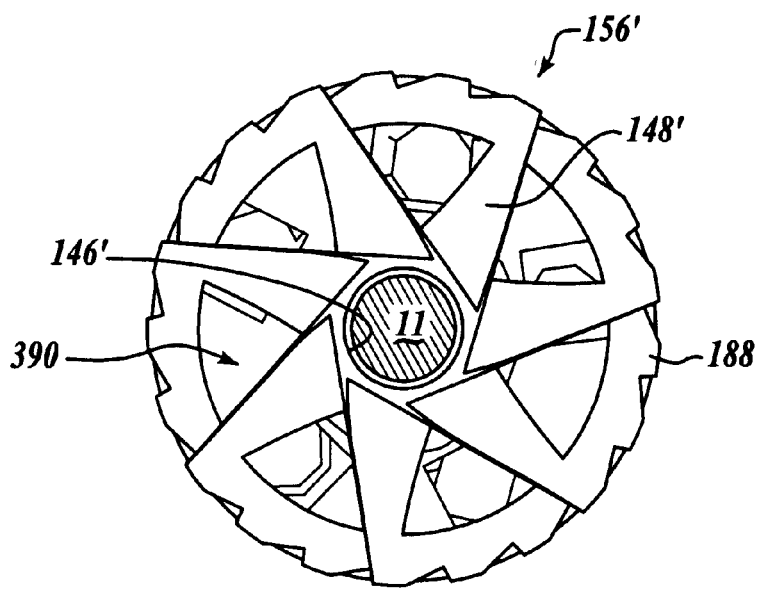
FIG. 12B provides a front perspective of the fixed diameter distal cutter illustrated in FIG. 12A.
Figure 13A:
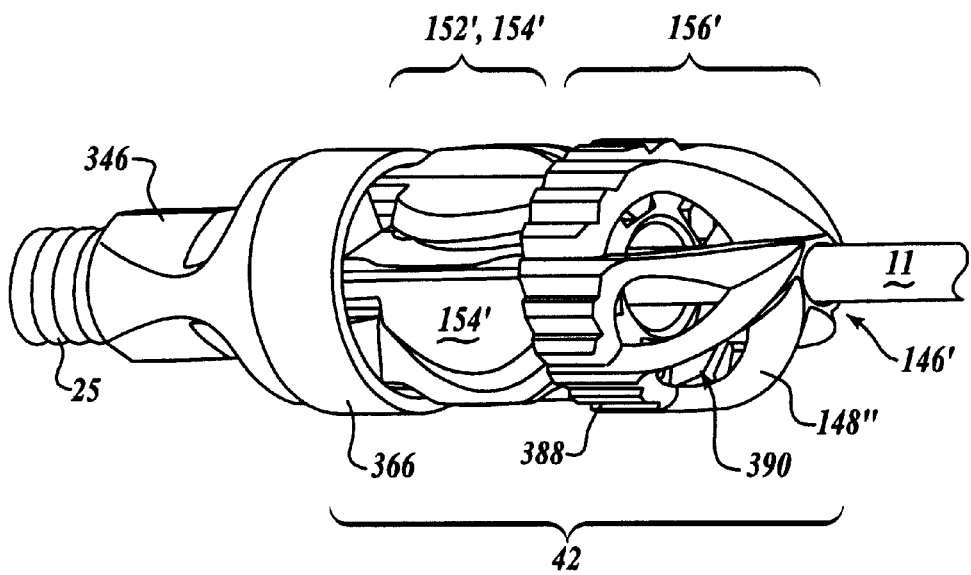
FIG. 13A shows an alternative embodiment of an expandable cutting assembly in the contracted configuration.
Figure 13B:
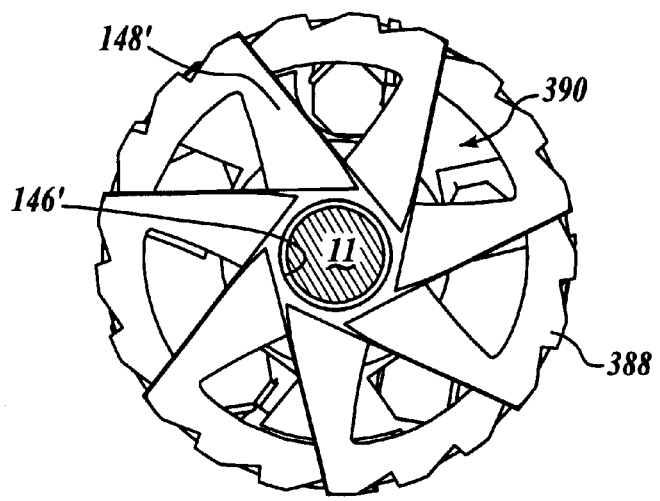
FIG. 13B provides a front perspective of the alternative embodiment illustrated in FIG. 13A.
Figure 14A:
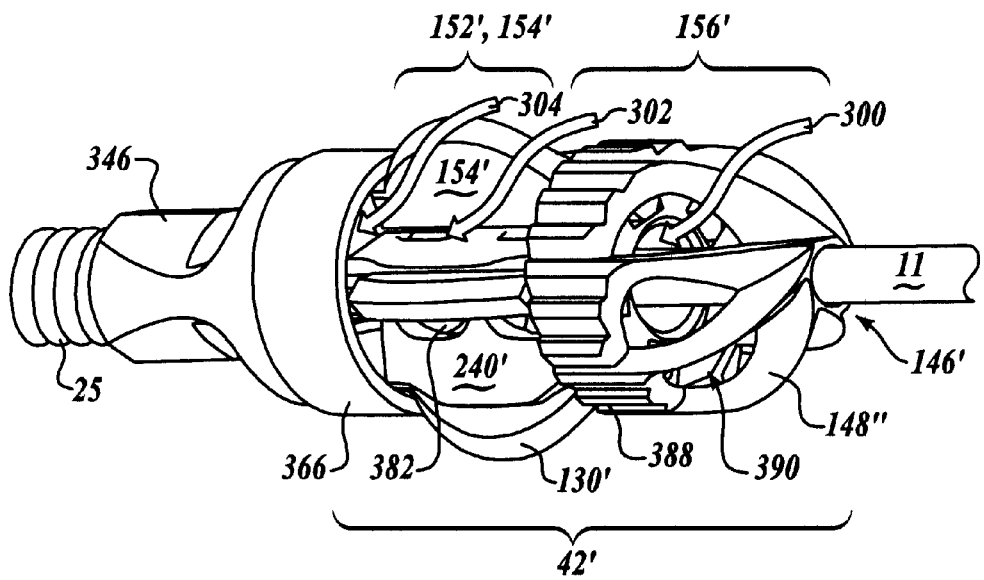
FIG. 14A shows an alternative embodiment of an expandable cutting assembly in the expanded configuration.
Figure 14B:
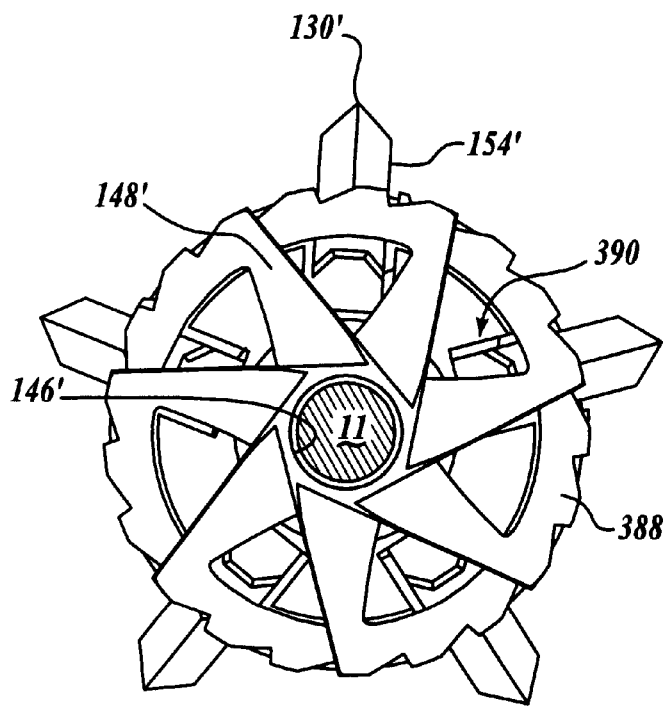
FIG. 14B provides a front perspective of the alternative embodiment illustrated in FIG. 14A.

The embodiment depicted in FIGS. 8–14B has a number of uniquely distinguishing features. As shown in FIGS. 9, 10 and 11, central block 152' may be fitted with any suitable number of cutting members 154', such as 8 or less. This preferred embodiment shows a central block having 5 cutting members, but, depending upon the application and overall dimensions of the cutting assembly, greater or fewer than 5 cutting elements may be employed. FIG. 11 shows central block 152' having a plurality of receiving slots 380 for receiving rod sections 124' of cutting members 154'. Cutting members 154' may be formed from interconnected rod and blade members, or preferably machined from one integral piece. As with the previous embodiment, cutting members 154' are provided with beveled edges 130', such that the principles of differential cutting apply. It is understood that any suitable differential cutting angle may be utilized for beveled edge 130' in addition to those depicted in the figures. A central aperture 136' is provided running along the longitudinal axis of central block 152' to permit free axial translation of guide wire 11 and/or other components, as well as serve as a conduit for aspiration and infusion. A plurality of ports 382 are provided in central block 152' which are continuous with central aperture 136' and lumen of flexible conduit catheter 342, 94', further providing aspiration capabilities to cutting assembly 42'. This particular embodiment provides a greater number of ports 382 in central block 152', thereby increasing aspiration and infusion efficiency.

Distal face 134' of central block 152' is fixedly connected to proximal face 160' of fixed diameter distal cutter 156' by any conventional methods, such as by welding, preferably laser welding, soldering, brazing, adhesive bonds and the like. As more clearly illustrated in FIGS. 12A and 12B, distal cutter 156' is generally of tapered, oblong, conical or frusto-conical design, or any suitably balanced configuration, and is provided with a plurality of raised "arch-like" cutting flutes or blades 148' radiating from central aperture 146' to body 388 of distal cutter 156'. As with all cutting members, blades and fixed diameter distal cutters described herein, this particular embodiment of a distal cutter also operates by differential cutting. Additionally, proximal and distal aspects of cutting flutes or blades 148' may be chamfered to render them atraumatic.

Distal cutter 156' is provided with a plurality of port-like cutouts for aspiration and infusion. In the context of this particular embodiment, port-like cutouts may also be referred to as ports. Each pair of cutting flutes 148' are cut away to provide an aspiration cutout 390, which form an internal cavity that is continuous with central aperture 136' of central block. This arrangement provides an aspiration and infusion conduit to the most distal end of expandable cutter 42'. The design and arrangement of cutting flutes 148', and aspiration cutouts 390 create an open configuration providing substantially maximal cutout surface area, which allow a greater volume of material to be aspirated from the situs of operation. In addition, distal cutter 156' may have any sort of cutting and/or grinding elements 394 associated with body 388 of distal cutter 156' to further facilitate removal of occlusive material.

Similar to embodiments previously described, FIGS. 13A to 14B illustrate cutting assembly 42' in a contracted and expanded configuration, respectively. Cutting members 154' freely rotate within recesses 380 of central block 154' and, depending on the direction of rotation, rotate from a tangential orientation, in which blade sections of cutting members engage respective support faces 140' (i.e., contracted configuration) to a radial orientation in which blade sections of cutting members 154' are in contact with stop faces 142' of central block 152' (i.e., expanded configuration). Stop faces 142' check rotational movement of blade members and provide support while operating in the expanded configuration.

The same general principles of operation described above apply to the embodiment depicted in FIGS. 8–14B. Notably, this alternative embodiment provides a fixed diameter distal cutter 156' having cutting flutes 148' that immediately engage occlusive material. Additionally, the alternative embodiment provides a comparatively large aspiration conduit area by virtue of the large aspiration cutouts or ports 390. During aspiration, aspirate and particulates are drawn through aspiration cutouts, or ports 390 of distal cutter 156', ports 382 of central block 152', as well as spaces between central block 152' and proximal cap 366, as depicted by arrows 400, 402 and 404, respectively.

It will be understood that the foregoing discussion merely illustrative of the invention and its principles. However, modifications and variations in the details of the disclosure will occur to those skilled in the art to which this invention relates and still remain within the scope and principles of the invention. It will be understood that obvious variations and modifications thereof that may be made by those skilled in the art are intended to be included within the spirit and purview f this application and the scope of the appended claims.

We claim:

1. An intralumenal material removal system comprising: a drive shaft that is rotatable and translatable; a drive system operably coupled to the drive shaft in proximity to its proximal end for rotating the drive shaft at rotational speeds in excess of 500 rpm; a hollow sheath having a diameter larger than a drive shaft diameter and forming a lumen between an inner surface of the sheath and an outer surface of the drive shaft; and a cutter assembly mounted at a distal end of the drive shaft, the cutter assembly comprising a plurality of material removal ports in communication with the lumen, a distal fixed diameter cutter having a plurality of cutting blades, and a proximal, expandable diameter cutter.

2. The system of claim 1, wherein the drive system operably coupled to the drive shaft in proximity to its proximal end is selectively bi-directional and is capable of selectively rotating the drive shaft in opposite directions.

3. The system of claim 1, wherein the proximal cutter has a first diameter when rotated in a first direction and a second diameter, larger than the first diameter, when rotated in a second direction opposite the first direction.

4. The system of claim 1, wherein the drive shaft is flexible and hollow, and comprises a first longitudinal section having a predominantly left-lay helical configuration, and a second longitudinal section adjoining the first section and having a predominantly right-lay helical configuration.

5. The system of claim 1, additionally comprising an advancer system for axially displacing the drive shaft and cutter assembly.

6. The system of claim 1, additionally comprising a flexible guidewire.

7. The system of claim 1, additionally comprising a magnetic coupler for operably coupling the drive system to the drive shaft.

8. The system of claim 1, additionally comprising a retainer assembly associated with the drive shaft and hollow sheath.

9. The system of claim 1, additionally comprising a retainer assembly associated with the drive shaft and hollow sheath located an operable distance from the cutter assembly.

10. An intralumenal material removal system comprising: a drive shaft that is rotatable and translatable; a drive system operably coupled to the drive shaft in proximity to its proximal end for rotating the drive shaft at rotational speeds in excess of 500 rpm; and a cutter assembly mounted at a distal end of the drive shaft, the cutter assembly comprising a plurality of cutting blades and a plurality of ports in communication with the lumen, wherein the drive shaft is flexible and hollow and comprises adjoining sections along a longitudinal axis having differently oriented helical configurations, at least one section having a predominantly left-lay helical configuration and at least one section having a predominantly right-lay helical configuration.

11. The system of claim 10, wherein the drive shaft comprises adjoining sections of left-lay and right-lay helical configurations of substantially equivalent length.

12. An intralumenal material removal system comprising: a drive shaft that is rotatable and translatable; a selectively bi-directional drive system operably coupled to the drive shaft in proximity to its proximal end for rotating the drive shaft at rotational speeds in excess of 500 rpm; and an expandable cutter assembly mounted at a distal end of the drive shaft, the expandable cutter assembly comprising a plurality of cutting blades, wherein the expandable cutter assembly has a first diameter when rotated in a first direction and a second diameter, larger than the first diameter, when rotated in a second direction opposite the first direction.

13. The system of claim 12, wherein the material removal system additionally comprises a plurality of material removal ports in communication with the lumen.

14. The system of claim 12, wherein the material removal system comprises a plurality of cutter blades that are configured to operate using the principle of differential cutting.

15. The system of claim 12, wherein the material removal system comprises a plurality of cutting blades pivotable on axes parallel to a central longitudinal axis of the cutter assembly.

16. The system of claim 12, additionally comprising a hollow sheath having a diameter larger than a drive shaft diameter and forming a lumen between an inner surface of the sheath and an outer surface of the drive shaft, and an aspiration source in communication with the lumen.

17. The system of claim 12, additionally comprising an advancer system for axially displacing the drive shaft and cutter assembly.

18. The system of claim 12, additionally comprising a flexible guidewire.

19. The system of claim 12, additionally comprising a magnetic coupler for operably coupling the drive system to the drive shaft.

20. A method for removing material from the interior of a lumen using a material removal system having a fixed diameter material removal device and an adjustable diameter material removal device, comprising: rotating the material removal system in a first direction while advancing it through material to be removed in a first pass in which the fixed diameter material removal device is the primary material remover, translating the material removal system in an antegrade direction for a subsequent pass, and rotating the material removal system in a second direction, opposite the first direction, while advancing it through the material to be removed in a subsequent pass in which the adjustable diameter material removal device is in an expanded condition and is the primary material remover.

21. An intralumenal material removal system comprising: a drive shaft that is rotatable and translatable; a drive system operably coupled to the drive shaft in proximity to its proximal end for rotating the drive shaft at rotational speeds in excess of 500; a hollow sheath having a diameter larger than a drive shaft diameter and forming a lumen between an inner surface of the sheath and an outer surface of the drive shaft; and a cutter assembly mounted at a distal end of the drive shaft, the cutter assembly comprising a plurality of cutting blades pivotable on axes parallel to a central longitudinal axis of the cutter assembly.

22. An intraluminal material removal system according to claim 2, additionally comprising material removal ports in communication with the lumen and in proximity to the cutting blades.

23. An intraluminal material removal system according to claim 21, wherein the drive system is selectively bi-directional.

24. An intraluminal material removal system according to claim 21, wherein the cutting blades have beveled edges.

25. An intraluminal material removal system according to claim 21, wherein the cutting blades operate according to the principle of differential cutting.

26. The system of claim 21, comprising eight or fewer cutting blades.

27. The system of claim 21, wherein the cutter assembly is adjustable to different diameters by positioning the pivotable cutting blades in a first smaller diameter condition and a second larger diameter condition, and additionally comprises raised spines having a stop face to contact and to support the pivotable cutting blades when in the first diameter condition.

28. The system of claim 27, wherein the raised spines additionally include a support face to contact the blades when in the second diameter condition.

* * * * *

UNITED STATES PATENT AND TRADEMARK OFFICE
CERTIFICATE OF CORRECTION

PATENT NO. : 6,565,588 B1
DATED : May 20, 2003
INVENTOR(S) : Thomas J. Clement, Edward I. Wulfman and Craig E. Lawson It is certified that error appears in the above-identified patent and that said Letters Patent is hereby corrected as shown below:

Column 20,
Line 60, replace "claim 2" with -- claim 21 --

Signed and Sealed this

Eighteenth Day of May, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,565,588 B1
DATED : May 20, 2003
INVENTOR(S) : Thomas J. Clement, Edward I. Wulfman and Craig E. Lawson It is certified that error appears in the above-identified patent and that said Letters Patent is hereby corrected as shown below:

Column 19,
Line 59, replace "communication with the lumen, wherein" with -- communication with a lumen communicating between the ports and a proximal end of the material removal system, wherein --
Line 66, replace "comprises adjoining sections" with -- comprises sections adjoining one another --

Column 20,
Line 14, replace "communication with the lumen." with -- communication with a lumen communicating between the ports and a proximal end of the material removal system. --

Signed and Sealed this

First Day of February, 2005

JON W. DUDAS
*Director of the United States Patent and Trademark Office*